United States Patent [19]

Harrison et al.

[11] 4,356,325

[45] Oct. 26, 1982

[54] PROCESS FOR PREPARATION OF ACETYLENE TERMINATED SULFONES, OLIGOMERS AND PRECURSORS THEREFOR

[75] Inventors: James J. Harrison, Glenshaw; Edward T. Sabourin, Allison Park; Charles M. Selwitz, Monroeville, all of Pa.

[73] Assignee: Gulf Research & Development Company, Pittsburgh, Pa.

[21] Appl. No.: 211,318

[22] Filed: Nov. 28, 1980

[51] Int. Cl.$^3$ .................. C07C 147/10; C07C 147/12; C07C 147/06
[52] U.S. Cl. ...................................... 568/33; 564/430
[58] Field of Search ........,................................. 568/33

[56] References Cited

U.S. PATENT DOCUMENTS

| | | | |
|---|---|---|---|
| 3,647,751 | 3/1972 | Darsow | 568/33 X |
| 3,830,781 | 8/1974 | Leslie et al. | 568/33 X |
| 3,917,715 | 11/1975 | Leslie et al. | 568/33 |
| 4,022,746 | 5/1977 | Kovar et al. | 260/30.2 |
| 4,051,109 | 9/1977 | Barr et al. | 568/33 X |
| 4,065,437 | 12/1977 | Blinne et al. | 568/33 X |
| 4,108,926 | 8/1978 | Arnold et al. | 260/874 |
| 4,128,588 | 12/1978 | Sabourin et al. | 260/645 |
| 4,131,625 | 1/1979 | Arnold et al. | 260/607 AR |

FOREIGN PATENT DOCUMENTS

1195704  6/1970  United Kingdom ................. 568/33

OTHER PUBLICATIONS

Smayn & Marvel, Journal of Polymer Science: Polymer Chemistry Edition, vol. 13, 1095–1106 (1975).
Loughran & Arnold, ACS Preprints Polymer Div., vol. 21, No. 1, Mar. 1980.
Kovar, Ehlers and Arnold, Journal of Polymer Science: Polymer Chemistry Edition, vol. 15, 1081–1095 (1977).
Rose, Polymer vol. 15, Jul. 1974, 456–465.
Johnson, Farnham, Clendinning, Hale and Merrian, Journal of Polymer Science: Part A.1, vol. 5, 2375–2398 (1967).
Maximovich, Lockerby, Arnold and Loughran, Society for the Advancement of Materials and Process Engineering, National SAMPE Symposium and Exhibition 23rd, 1978.

*Primary Examiner*—John Doll
*Attorney, Agent, or Firm*—Roylance, Abrams, Berdo & Farley

[57] ABSTRACT

Acetylene terminated sulfones and oligomers thereof are prepared by reacting a sulfonyldiphenol with a material selected from the group consisting of a meta-dibromobenzene, a para-dibromobenzene and mixtures thereof in the presence of a potassium base to form a bis-bromophenoxydiphenyl sulfone, which is reacted with a substituted terminal acetylene compound containing at least three carbon atoms and an hydroxy group on the carbon atom adjacent to the acetylene group to form an hydroxy-acetylene terminated phenoxydiphenyl sulfone, which is then subjected to base catalyzed cleavage to form the desired acetylene terminated sulfones and oligomers. An hydroxy-arylacetylene terminated sulfone is prepared by reacting a sulfonyldiphenyl with a material selected from the group consisting of meta-dibromobenzene para-dibromobenzene and mixtures thereof in the presence of a sodium base. The resulting hydroxyphenylbromophenoxyphenyl sulfone can be: (1) reacted with a substituted terminal acetylene compound to form an hydroxy-arylacetylene terminated sulfone which in turn can be reacted with a dinitrofluorobenzene to form a dinitro-acetylene terminated sulfone which in turn can be reacted with sodium dithionite and sodium hydroxide to form a diaminoacetylene terminated sulfone; (2) reacted with a dibromobenzene to form a bis-bromophenoxydiphenyl sulfone; or (3) reacted with a bis-bromophenoxydiphenyl sulfone to form an oligomeric bromophenoxydiphenyl sulfone, which can be used to form an oligomeric actylene terminated sulfone. Metal contaminants, such as palladium and copper, used in the preparation of the acetylene terminated sulfones are removed by admixing the metal contaminated sulfone with a hydrogen halide and then contacting the admixture with an amino compound to complex the metal contaminant.

145 Claims, No Drawings

PROCESS FOR PREPARATION OF ACETYLENE TERMINATED SULFONES, OLIGOMERS AND PRECURSORS THEREFOR

The invention herein described was made in the course of or under a contract or subcontract thereunder with the United States Air Force.

FIELD OF THE INVENTION

The present invention relates to the production of acetylene terminated sulfones, oligomers of such sulfones, precursor compounds used for producing such acetylene terminated sulfones, and to the sulfones, oligomers and precursor compounds produced thereby.

DESCRIPTION OF THE PRIOR ART

Epoxy matrix composites have been widely used in aerospace products. However, epoxy matrix systems are sensitive to moisture. Extended exposure to high humidity reduces the mechanical properties of cured epoxy systems at elevated temperatures. Accordingly, there has been a growing interest in polymers that could replace epoxies and which are significantly less sensitive to moisture but which retain the desirable characteristics of the epoxies. Acetylene terminated sulfone oligomers exhibit good resistance to moisture, a low-viscosity melt phase at temperatures below a reasonably low cure temperature, and other properties which make it a strong candidate as an epoxy substitute.

The preparation of the acetylene terminated sulfone, 4,4′-bis-(3-ethynylphenoxy)diphenylsulfone, utilizing m-hydroxyphenylacetylene is described in U.S. Pat. Nos. 4,131,625 and 4,108,926 to Arnold et al. However, m-hydroxyphenylacetylene is difficult to synthesize and expensive to produce.

SUMMARY OF THE INVENTION

Surprisingly, and in accordance with the present invention, it has been found that novel acetylene terminated sulfones can be prepared by an Ullmann-type condensation involving the reaction of relatively inexpensive sulfonyldiphenol with a material selected from the group consisting of a meta-dibromobenzene, a para-dibromobenzene and mixtures thereof, in the presence of a potassium base under conditions to produce a bis-bromophenoxydiphenyl sulfone. The bis-bromophenoxydiphenyl sulfone is thereafter reacted with a substituted terminal acetylene compound containing at least three carbon atoms and an hydroxy group on the carbon atom adjacent to the acetylene group, so as to produce the corresponding hydroxy-acetylene terminated phenoxydiphenyl sulfone which, in turn, may be converted to the desired acetylene terminated sulfone by base catalyzed cleavage.

It was quite unexpected that only when the potassium base is utilized will the reaction produce a bis-bromophenoxydiphenyl sulfone, since Ullmann-type condensation reactions do not depend so critically upon the nature of the particular alkali metal salt used. Moreover, the process of the present invention further distinguishes typical Ullmann reactions which require a pyridine cosolvent. As will be hereinafter demonstrated, the present process can be conducted in the presence or absence of a pyridine solvent. Thus, the present process can eliminate the usual environmental problems associated with a pyridine-type solvent.

According to one aspect of the present invention, a novel acetylene terminated sulfone precursor, namely, a bis-bromophenoxydiphenyl sulfone, is produced.

According to another aspect of the present invention, the bis-bromophenoxydiphenyl sulfone is reacted with a substituted terminal acetylene compound to produce a novel hydroxy-acetylene terminated sulfone which, in turn, can be converted to novel acetylene terminated sulfones by base catalyzed cleavage.

According to still another embodiment of the present invention, it has been found that the reaction of the sulfonyldiphenol with the dibromobenzene produces novel oligomeric bromophenoxydiphenyl sulfones which, in turn, can be reacted with a substituted terminal acetylene compound to provide oligomeric acetylene terminated sulfones which have been found to be extremely valuable in preventing crystallization of acetylene terminated sulfones during fabrication into polymeric articles.

According to still another aspect of the present invention, a sulfonyldiphenol is reacted with a dibromobenzene in the presence of a sodium base to produce a hydroxyphenylbromophenoxyphenyl sulfone which can be reacted with a substituted terminal acetylene compound to produce a novel hydroxy-arylacetylene terminated sulfone.

According to a further aspect of the present invention, acetylene terminated sulfones can be produced having a reduced tendency to crystallize, thus providing greater ease in fabrication of acetylene terminated sulfone polymers.

According to another embodiment of the present invention, the hydroxyphenylbromophenoxy-phenyl sulfone can be reacted with the bis-bromophenoxydiphenyl sulfone of the present invention to produce novel oligomeric bromophenoxydiphenyl sulfones.

According to another aspect of the present invention, the hydroxy-arylacetylene terminated sulfones of the present invention can be used to prepare diamino-acetylene terminated sulfones useful in the preparation of acetylene-terminated polyphenylquinoxaline resin.

According to still another embodiment of the present invention, a process is provided for removing catalyst metal contaminants, such as palladium and copper, used in the production of acetylene terminated sulfones and oligomers thereof, which process avoids the use of relatively expensive metal adsorbents, such as silica gel, alumina or the like.

DESCRIPTION OF THE PREFERRED EMBODIMENTS

As previously mentioned, the process of the present invention involves the reaction of a sulfonyl diphenol with a meta- and/or para-dibromobenzene in the presence of a potassium base.

Any suitable sulfonyl diphenol can be employed in the aforesaid reaction, such as those having the formula:

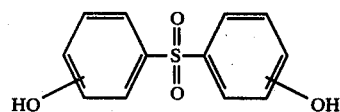

Examples of such compounds include: 3,3′-sulfonyldiphenol; 3,4′-sulfonyldiphenol; 3,2′-sulfonyldiphenol;

2,2'-sulfonyldiphenol; 4,4'-sulfonyldiphenol; 4,2'-sulfonyldiphenol, and the like.

The preferred sulfonyl diphenol is where the hydroxy groups are para with respect to the sulfur moiety, i.e., 4,4'-sulfonyl diphenol.

Suitable dibromobenzenes are those in which the bromine atoms are in either a meta- or para-configuration. The use of an ortho-dibromobenzene is not desired and such compound is considered to be an impurity in the present process, since unsatisfactory products will result. Suitable dibromobenzenes include those having the formula:

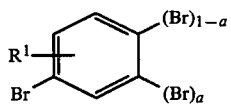

wherein a is the integer 0 or 1, and $R^1$ is hydrogen; saturated or unsaturated, straight or branched chain alkyl radicals having from about one to about 20 carbon atoms, preferably from about one to about 10 carbon atoms with lower alkyl radicals, e.g., methyl, ethyl, propyl and butyl being especially preferred; aryl radicals having from about six to about 20 carbon atoms, preferably from about six to about 10 carbon atoms, e.g., phenyl and naphthyl; alkenyl radicals having from about one to about 20 carbon atoms, preferably lower alkenyl of from about one to about 5 carbon atoms; cycloalkyl radicals having from about three to about 20 carbon atoms, preferably from about three to about 10 carbon atoms; and aralkyl and alkaryl radicals having from about six to about 20 carbon atoms, preferably from about six to about 12 carbon atoms.

The dibromobenzene nucleus can be substituted with any suitable radical, $R^1$, provided that it does not interfere with the desired reaction between the sulfonyl diphenol and the dibromobenzene.

The sulfonyl diphenol and the dibromobenzene react to form a bis-bromophenoxydiphenyl sulfone as follows:

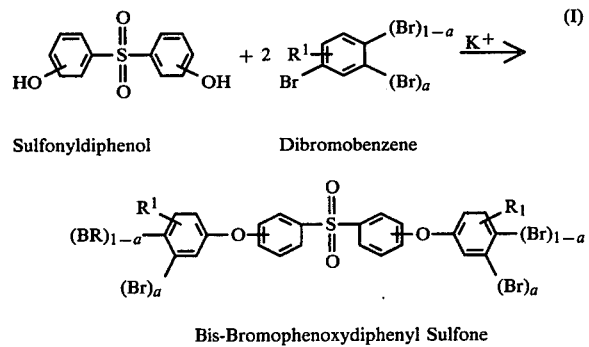

Sulfonyldiphenol      Dibromobenzene

Bis-Bromophenoxydiphenyl Sulfone wherein a and $R^1$ are as previously defined.

Especially preferred bis-bromophenoxydiphenyl sulfones are those having the formula:

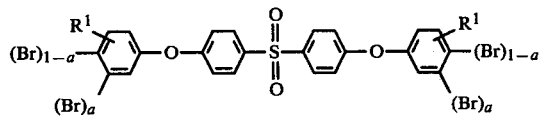

wherein a and $R^1$ are as previously defined.

Examples of suitable bis-bromophenoxydiphenyl sulfones include:
4,4'-bis-(3-bromophenoxy)diphenyl sulfone,
4,4'-bis-(4-bromophenoxy)diphenyl sulfone,
4-(3-bromophenoxy)-4'-(4-bromophenoxy)diphenyl sulfone,
4,4'-bis-(3-bromophenoxy-2-methyl)diphenyl sulfone,
4,4'-bis-(4-bromophenoxy-2-methyl)diphenyl sulfone,
4-(3-bromophenoxy-2-methyl)-4'-(4-bromophenoxy-2-methyl)diphenyl sulfone,
4,4'-bis-(3-bromo-5-methylphenoxy)diphenyl sulfone,
4-(3-bromo-5-methylphenoxy)-4'-(3-bromo-2-methylphenoxy)diphenyl sulfone,
4-(3-bromo-5-methylphenoxy)-4'-(4-bromo-2-methylphenoxy)diphenyl sulfone,
4,2'-bis-(3-bromophenoxy)diphenyl sulfone,
4,2'-bis-(4-bromophenoxy)diphenyl sulfone,
4-(3-bromophenoxy)-2'-(4-bromophenoxy)diphenyl sulfone,
4,2'-bis-(3-bromophenoxy-2-methyl)diphenyl sulfone,
4,2'-bis-(4-bromophenoxy-2-methyl)diphenyl sulfone,
4-(3-bromophenoxy-2-methyl)-2'-(4-bromophenoxy-2-methyl)diphenyl sulfone,
4,2'-bis-(3-bromo-5-methylphenoxy)diphenyl sulfone,
4-(3-bromo-5-methylphenoxy)-2'-(3-bromo-2-methylphenoxy)diphenyl sulfone,
4-(3-bromo-5-methylphenoxy)-2'-(4-bromo-2-methylphenoxy)diphenyl sulfone;
4,4'-bis-(3-bromophenoxy-2-phenyl)diphenyl sulfone,
4,4'-bis-(4-bromophenoxy-2-phenyl)diphenyl sulfone,
4-(3-bromophenoxy-2-phenyl)-4'-(4-bromophenoxy-2-phenyl)diphenyl sulfone,
4,4'-bis-(3-bromo-5-phenylphenoxy)diphenyl sulfone,
4-(3-bromo-5-phenylphenoxy)-4'-(3-bromo-2-phenylphenoxy)diphenyl sulfone,
4-(3-bromo-5-phenylphenoxy)-4'-(4-bromo-2-phenylphenoxy)diphenyl sulfone, and the like.

As previously indicated, it was surprising to find that Reaction (I) will only take place in the presence of a potassium base, such as potassium hydroxide, since Ullmann condensations do not depend so critically upon the alkali metal salt used. It has been found that when a potassium base is used, a potassium di-salt of the sulfonyldiphenol is formed, and this resulting potassium salt then displaces the bromine in the dibromobenzene to form the bis-bromophenoxydiphenyl sulfone. Any suitable potassium base can be used, for example, potassium hydroxide, potassium carbonate, potassium tertiary butoxide, or the like. The use of a sodium base results in a different product.

Reaction (I) preferably takes place in the presence of a copper catalyst, such as copper salt, e.g., copper stearate, copper acetate, copper acetonylacetonate, cuprous bromide, preferably cuprous chloride or cuprous iodide. Usually, the amount of copper salt utilized is between about 0.1 and about 10 mole percent based on the dibromobenzene, preferably between about 1.0 and 5.0 mole percent based on the dibromobenzene.

Unlike the usual Ullmann condensation reactions, Reaction (I) does not require a pyridine solvent, and such reaction can be conducted in the presence of other suitable solvents, including dimethylsulfoxide, N-methylpyrolidone, bis-methoxy ethoxy diethyl ether, and the like. A preferred solvent is tetrahydrothiophene 1,1-dioxide, known as sulfolane.

The reaction of the sulfonyldiphenol with the dibromobenzene can be conducted under any suitable conditions easily determined by those skilled in this art. The reaction conditions should be such that the solvent chosen is maintained in the liquid phase. The normal reaction pressure is atmospheric; however, increased pressures of up to 250 psig (1.7 MPa) or higher can be employed. Suitable temperatures include those in the range of between about 100° and 250° C., preferably between about 140° and 200° C. The reaction time is somewhat dependent upon the particular charge stock and catalyst chosen and, of course, upon the reaction temperature. Suitable reaction times include from about one to about 150 hours, but are more usually from 3 to 24 hours.

The bis-bromophenoxydiphenyl sulfone produced in Reaction (I) can be reacted with a substituted terminal acetylene compound to provide an hydroxy-acetylene terminated phenoxydiphenyl sulfone. The substituted terminal acetylene compound contains at least three carbon atoms and an hydroxy group on the carbon atom adjacent the acetylene group. Preferred substituted terminal acetylene compounds are those having the formula:

HC≡C—Z wherein Z represents the moiety:

wherein $R^2$ and $R^3$ can be the same or different and are selected from the group consisting of hydrogen, lower alkyl groups having from one to 4 atoms, phenyl, substituted phenyl; or where $R^2$ and $R^3$ together with the carbon atom to which they are attached form a saturated 5- or 6-membered ring. The preparation of these compounds is well known in the art and forms no part of the subject invention. Suitable acetylenic compounds include the following: 3-methylbutyn-3-ol; 2-methyl-3-butyn-2-ol; 3-methyl-1-pentyn-3-ol; 3-ethyl-1-pentyn-3-ol; 2-phenyl-3-butyn-2-ol; 1-ethynylcyclohexanol; and 1-ethynylcyclopentanol.

The bis-bromophenoxydiphenyl sulfone and the substituted terminal acetylene compound are reacted as follows:

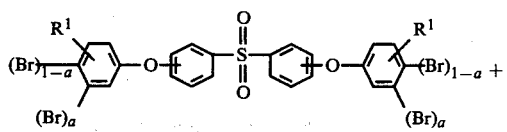

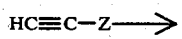

(II)

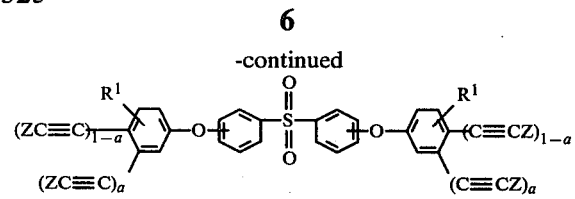

wherein a and $R^1$ are as previously defined, and Z represents the moiety:

wherein $R^2$ and $R^3$ can be the same or different and are selected from the group consisting of hydrogen, lower alkyl groups having from one to 4 carbon atoms, phenyl, substituted phenyl; or when $R^2$ and $R^3$ are taken together with the carbon atom to which they are attached form a 5- or 6-membered carbon atom ring.

The preferred hydroxy-acetylene terminated, phenoxy-diphenyl sulfones produced in Reaction (II) are those having the formula:

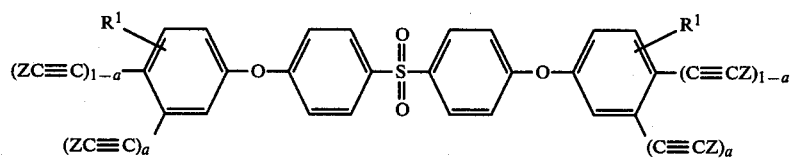

wherein a, $R^1$ and Z are as previously defined.

Usually the bis-bromophenoxydiphenyl sulfone is reacted with the terminal acetylene compounds in a molar ratio of about 1:2, but suitable molar ratios include those from 1:0.5 to 1:100 and are more preferably from 1:2 to 1:5.

The reaction of the bis-bromophenoxydiphenyl sulfone with the terminal acetylenic compounds defined above occurs in the presence of a dialkyl or trialkyl amine solvent and a complex catalyst system. The amine solvent can suitably have the formula:

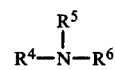

where $R^4$, $R^5$ and $R^6$ can be the same or different and are selected from the group consisting of hydrogen and lower alkyl groups having from one to 4 carbon atoms, with the proviso that no more than one of said R groups can be hydrogen. Suitable solvents include but are not limited to dimethylamine, trimethylamine, diethylamine, triethylamine, ethylpropylamine, ethylbutylamine and dibutylamine.

The catalyst employed is a complex palladium salt containing two halogen moieties, where the halogen is selected from the group consisting of bromine, iodine and chlorine, and two trisubstituted phosphine moieties where the constituents are selected from phenyl, alkyl groups having from one to 4 carbon atoms, and substituted phenyl groups. A suitable palladium complex has the formula:

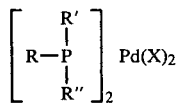

where X is bromine, iodine or chlorine, and R, R' and R'' are the same or different and are selected from the group consisting of phenyl, alkyl groups having from one to 4 carbon atoms and substituted phenyl groups. The substituents on the phenyl groups can include alkyl groups having from one to 4 carbon atoms, alkoxy groups having one to 4 carbon atoms, and halogen. A suitable list of representative palladium complex salts which can be employed in the process of this invention include: bis(triphenylphosphine)palladium dichloride; bis(triphenylphosphine)palladium dibromide; bis(tri-n-butylphosphine)palladium dichloride; bis(tri-t-butylphosphine)palladium dichloride; bis-(tri-i-butylphosphine)palladium dichloride; bis(triethylphosphine)palladium dichloride; bis(tripropylphosphine)palladium dichloride; bis(tritolylphosphine)palladium dichloride; bis(trianisylphosphine)palladium dichloride; bis(tri(chlorophenyl)phosphine)palladium dichloride; and bis(tri(bromophenyl)phosphine)palladium dichloride.

A promoter for the catalyst system is also employed, and this promoter comprises cuprous salts, such as cuprous iodide, cuprous chloride, copper stearate, copper acetate, copper acetonylacetonate and cuprous bromide. Usually the amount of the promoter is very small, and suitable amounts of promoter include a molar ratio of promoter to palladium catalyst of from 0.5:1 to 20:1, preferably from 1:1 to 5:1. The amount of the palladium catalyst employed in the reaction is usually from 0.01 to 1.0 mole percent based on the bis-bromophenoxydiphenyl sulfone and is more preferably from 0.02 to 0.05 mole percent based on the bisbromophenoxydiphenyl sulfone.

The reaction of the bis-bromophenoxydiphenyl sulfone with the acetylene terminated compound (Reaction II) is actually a substitution-type reaction, and the reaction conditions to employ are relatively mild and include a temperature from about 20° to 200° C. and more preferably from 50° to 125° C. However, it is considered that the reaction conditions are not critical, and the precise reaction conditions to employ would be obvious to one having ordinary skill in the art. The reaction conditions should be such that the solvent chosen is maintained in the liquid phase. The normal reaction pressure is atmosphereic; however, increased reaction pressures of up to 250 psig (1.7 MPa) or higher can be employed. The reaction time to employ is somewhat dependent on the particular charge stock and catalyst chosen and, of course, on the reaction temperature. Usually the reaction time is from one hour to 150 hours but is more usually from 3 hours to 24 hours. Higher or lower reaction times can be employed for timing is not a critical parameter, but rather in many cases serves to increase the yield of the desired reaction product.

Examples of suitable hydroxy-acetylene terminated phenoxy-diphenyl sulfones produced in Reaction (II) include:

4,4'-bis-(3-(3-hydroxy-3-methylbutynyl)phenoxy)diphenyl sulfone,
4,4'-bis-(4-(3-hydroxy-3-methylbutynyl)phenoxy)diphenyl sulfone,
4-(3-(3-hydroxy-3-methylbutynyl)phenoxy)-4'-(4-(3-hydroxy-3-methylbutynyl)phenoxy)diphenyl sulfone,
4,4'-bis-(3-(3-hydroxy-3-methylbutynyl)-2-methylphenoxy)diphenyl sulfone,
4,4'-bis-(4-(3-hydroxy-3-methylbutynyl)-2-methylphenoxy)diphenyl sulfone,
4-(3-(3-hydroxy-3-methylbutynyl)-2-methylphenoxy)-4'-(4-(3-hydroxy-3-methylbutynyl)-2-methylphenoxy)diphenyl sulfone,
4,4'-bis-(3-(3-hydroxy-3-methylbutynyl)-5-methylphenoxy)diphenyl sulfone,
4-(3-(3-hydroxy-3-methylbutynyl)-5-methylphenoxy)-4'-(3-(3-hydroxy-3-methylbutynyl)-2-methylphenoxy)diphenyl sulfone,
4-(3-(3-hydroxy-3-methylbutynyl)-5-methylphenoxy)-4'-(4-(3-hydroxy-3-methylbutynyl)-2-methylphenoxy)diphenyl sulfone,
4,4'-bis-(3-(3-hydroxy-3-methylpentynyl)phenoxy)diphenyl sulfone,
4,4'-bis-(4-(3-hydroxy-3-methylpentynyl)phenoxy)diphenyl sulfone,
4-(3-(3-hydroxy-3-methylpentynyl)phenoxy)-4'-(4-(3-hydroxy-3-methylpentynyl)phenoxy)diphenyl sulfone,
4,4'-bis-(3-(3-hydroxy-3-ethylpentynyl)phenoxy)diphenyl sulfone,
4,4'-bis-(4-(3-hydroxy-3-ethylpentynyl)phenoxy)diphenyl sulfone,
4-(3-(3-hydroxy-3-ethylpentynyl)phenoxy)-4'-(4-(3-hydroxy-3-ethylpentynyl)phenoxy)diphenyl sulfone,
4,4'-bis-(3-(3-hydroxy-3-phenylbutynyl)phenoxy)diphenyl sulfone,
4,4'-bis-(4-(3-hydroxy-3-phenylbutynyl)phenoxy)diphenyl sulfone,
4-(3-(3-hydroxy-3-phenylbutynyl)phenoxy)-4'-(4-(3-hydroxy-3-phenylbutynyl)phenoxy)diphenyl sulfone,
4,4'-bis-(3-(2-(1-hydroxycyclohexyl)ethynyl)phenoxy)diphenyl sulfone,
4,4'-bis-(4-(2-(1-hydroxycyclohexyl)ethynyl)phenoxy)diphenyl sulfone,
4-(3-(2-(1-hydroxycyclohexyl)ethynyl)phenoxy)-4'-(4-(2-(1-hydroxycyclohexyl)ethynyl)phenoxy)diphenyl sulfone,
4,4'-bis-(3-(2-(1-hydroxycyclopentyl)ethynyl)phenoxy)diphenyl sulfone,
4,4'-bis-(4-(2-(1-hydroxycyclopentyl)ethynyl)phenoxy)diphenyl sulfone,
4-(3-(2-(1-hydroxycyclopentyl)ethynyl)phenoxy)-4'-(4-(2-(1-hydroxycyclopentyl)ethynyl)phenoxy)diphenyl sulfone,
4-(3-(3-hydroxy-3-methylpentynyl)phenoxy)-2'-(4-(3-hydroxy-3-methylpentynyl)phenoxy)diphenyl sulfone,
4,2'-bis-(3-(3-hydroxy-3-ethylpentynyl)phenoxy)diphenyl sulfone,
4,2'-bis-(4-(3-hydroxy-3-ethylpentynyl)phenoxy)diphenyl sulfone,
4-(3-(3-hydroxy-3-ethylpentynyl)phenoxy)-2'-(4-(3-hydroxy-3-ethylpentynyl)phenoxy)diphenyl sulfone,
4,2'-bis-(3-(3-hydroxy-3-phenylbutynyl)phenoxy)diphenyl sulfone,
4,2'-bis-(4-(3-hydroxy-3-phenylbutynyl)phenoxy)diphenyl sulfone,
4-(3-(3-hydroxy-3-phenylbutynyl)phenoxy)-2'-(4-(3-hydroxy-3-phenylbutynyl)phenoxy)diphenyl sulfone,
4,2'-bis-(3-(2-(1-hydroxycyclohexyl)ethynyl)phenoxy)diphenyl sulfone, 4,2'-bis-(4-(2-(1-hydroxycyclohexyl)ethynyl)phenoxy)-
diphenyl sulfone,
4-(3-(2-(1-hydroxycyclohexyl)ethynyl)phenoxy)-2'-(4-
(2-(1-hydroxycyclohexyl)ethynyl)phenoxy)diphenyl
sulfone,
4,2'-bis-(3-(2-(1-hydroxycyclopentyl)ethynyl)phenoxy)-
diphenyl sulfone,
4,2'-bis-(4-(2-(1-hydroxycyclopentyl)ethynyl)phenoxy)-
diphenyl sulfone,
4-(3-(2-(1-hydroxycyclopentyl)ethynyl)phenoxy)-2'-(4-
(2-(1-hydroxycyclopentyl)ethynyl)phenoxy)diphenyl
sulfone,
4,2'-bis-(3-(3-hydroxy-3-methylbutynyl)phenoxy)diphe-
nyl sulfone,
4,2'-bis-(4-(3-hydroxy-3-methylbutynyl)phenoxy)diphe-
nyl sulfone,
4-(3-(3-hydroxy-3-methylbutynyl)phenoxy)-2'-(4-(3-
hydroxy-3-methylbutynyl)phenoxy)diphenyl sulfone,
4,2'-bis-(3-(3-hydroxy-3-methylbutynyl)-2-methyl-
phenoxy)diphenyl sulfone,
4,2'-bis-(4-(3-hydroxy-3-methylbutynyl)-2-methyl-
phenoxy)diphenyl sulfone,
4-(3-(3-hydroxy-3-methylbutynyl)-2-methylphenoxy)-
2'-(4-(3-hydroxy-3-methylbutynyl)-2-methylphenox-
y)diphenyl sulfone,
4,2'-bis-(3-(3-hydroxy-3-methylbutynyl)-5-methyl-
phenoxy)diphenyl sulfone,
4-(3-(3-hydroxy-3-methylbutynyl)-5-methylphenoxy)-
2'-(3-(3-hydroxy-3-methylbutynyl)-2-methylphenox-
y)diphenyl sulfone,
4-(3-(3-hydroxy-3-methylbutynyl)-5-methylphenoxy)-
2'-(4-(3-hydroxy-3-methylbutynyl)-2-methylphenox-
y)diphenyl sulfone,
4,2'-bis-(3-(3-hydroxy-3-methylpentynyl)phenoxy)-
diphenyl sulfone,
4,2'-bis-(4-(3-hydroxy-3-methylpentynyl)phenoxy)-
diphenyl sulfone, and the like.

The hydroxy-acetylene terminated phenoxy-diphe-
nyl sulfone reaction mixture is subjected to a metals
removal operation for removal of the palladium and
copper metal contaminants. If the metals were not re-
moved, the resulting acetylene terminated sulfone
would cure at lower temperatures than desired and
make it difficult to fabricate the polymeric material into
the desired form. A suitable metals-removal system
involves the use of a combination of a hydrogen halide-
treatment step followed by a metals complexing step
using an amino compound, which system is hereinafter
described in detail.

The hydroxy-acetylene terminated phenoxy-diphe-
nyls sulfone produced in Reaction (II) is then subjected
to base catalyzed cleavage to form the desired acetylene
terminated sulfone as follows:

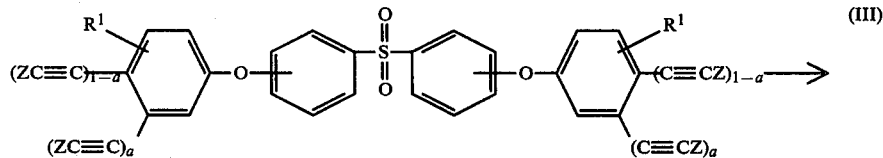

Hydroxy-acetylene Terminated Phenoxy-diphenyl Sulfone

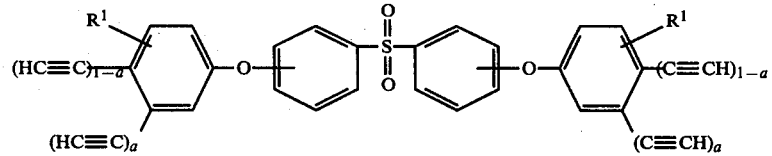

Acetylene Terminated Sulfone wherein a, $R^1$ and Z are as previously defined.

Base catalyzed cleavage is conducted under any suit-
able reaction conditions, such as a temperature in the
range of between about 70° and about 130° C., and
preferably between about 90° and 120° C., in the pres-
ence of a suitable base, such as potassium hydroxide or
sodium hydroxide for 0.5 to 10 hours, preferably 1 to 4
hours, for example. Potassium hydroxide is preferred.

Preferred acetylene terminated sulfones produced by
Reaction (II) are those having the formula:

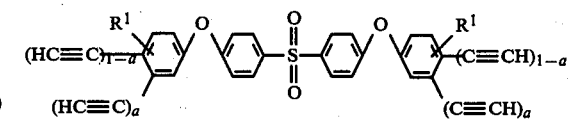

wherein a and $R^1$ are as previously defined.

Especially preferred acetylene terminated sulfones of
the present invention are meta, para and para, para
compounds having the structure:

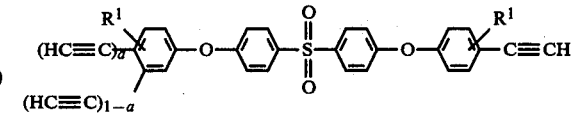

wherein a and $R^1$ are as previously defined.

Suitable acetylene terminated sulfones include:
4,4'-bis-(3-ethynylphenoxy)diphenyl sulfone,
4,4'-bis-(4-ethynylphenoxy)diphenyl sulfone,
4-(3-ethynylphenoxy)-4'-(4-ethynylphenoxy)diphenyl
sulfone,
4,4'-bis-(3-ethynyl-2-methylphenoxy)diphenyl sulfone,
4,4'-bis-(4-ethynyl-2-methylphenoxy)diphenyl sulfone,
4-(3-ethynyl-2-methylphenoxy)-4'-(4-ethynyl-2-methyl-
phenoxy)diphenyl sulfone,
4,4'-bis-(3-ethynyl-5-methylphenoxy)diphenyl sulfone,
4-(3-ethynyl-5-methylphenoxy)-4'-(3-ethynyl-2-methyl-
phenoxy)diphenyl sulfone,
4-(3-ethynyl-5-methylphenoxy)-4'-(4-ethynyl-2-methyl-
phenoxy)diphenyl sulfone,
4,2'-bis-(3-ethynylphenoxy)diphenyl sulfone, 4,2'-bis-(4-ethynylphenoxy)diphenyl sulfone,
4-(3-ethynylphenoxy)-2'-(4-ethynylphenoxy)diphenyl sulfone,
4,2'-bis-(3-ethynyl-2-methylphenoxy)diphenyl sulfone,
4,2'-bis-(4-ethynyl-2-methylphenoxy)diphenyl sulfone,
4-(3-ethynyl-2-methylphenoxy)-2'-(4-ethynyl-2-methylphenoxy)diphenyl sulfone,
4,2'-bis-(3-ethynyl-5-methylphenoxy)diphenyl sulfone,
4-(3-ethynyl-5-methylphenoxy)-2'-(3-ethynyl-2-methylphenoxy)diphenyl sulfone,
4-(3-ethynyl-5-methylphenoxy)-2'-(4-ethynyl-2-methylphenoxy)dipenyl sulfone,
4,4'-bis-(3-ethynyl-2-phenylphenoxy)diphenyl sulfone,
4,4'-bis-(4-ethynyl-2-phenylphenoxy)diphenyl sulfone,
4-(3-ethynyl-2-phenylphenoxy)-4'-(4-ethynyl-2-phenylphenoxy)diphenyl sulfone,
4,4'-bis-(3-ethynyl-5-phenylphenoxy)diphenyl sulfone,
4-(3-ethynyl-5-phenylphenoxy)-4'-(3-ethynyl-2-phenylphenoxy)diphenyl sulfone,
4-(3-ethynyl-5-phenylphenoxy)-4'-(4-ethynyl-2-phenylphenoxy)diphenyl sulfone, and the like.

The use of pure, symmetrical bis-bromophenoxydiphenyl sulfones containing a structure wherein the bromine and oxygen moieties are in a meta- configuration on both sides of the compound [e.g., 4,4'-bis-(3-bromophenoxy)diphenyl sulfone] for the production of acetylene terminated sulfones results in unwanted crystallization in the acetylene terminated sulfone product. Thus, a dibromobenzene mixture comprising, for example, 95% meta- and 5% para-dibromobenzene can be used in Reaction (I) with 4,4'-sulfonyldiphenol to produce a bis-bromophenoxydiphenyl sulfone mixture comprising meta, meta; meta, para; and para, para isomers thereof. A 70% meta- and 30% para-dibromobenzene can also be used. This is important because when a bromobenzene is brominated to form a dibromobenzene, the resulting mixture is likewise composed of approximately 70% meta- and 30% para-dibromobenzene. Thus, this dibromobenzene mixture can be used without purification in the process of the present invention. The use of such bis-bromophenoxydiphenyl sulfone mixture to produce acetylene terminated sulfones results in an acetylene terminated sulfone mixture having the same approximate composition of meta-meta, meta-para and para-para acetylene terminated sulfone isomers as in the bis-bromophenoxydiphenyl sulfone mixture. These mixtures are useful to avoid unwanted crystallization and permit easy fabrication of the acetylene terminated sulfones therefrom. Especially preferred bis-bromophenoxydiphenyl sulfones are those having a meta-para configuration, since the resulting corresponding acetylene terminated sulfones have the best properties.

According to another embodiment of the present invention, it has been found that the reaction of the sulfonyldiphenol with the dibromobenzene, as in Reaction (I), also produces polymeric materials having the formula:

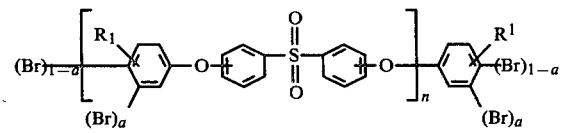

wherein n is 2 or 3 and a and $R^1$ are as previously defined.

The especially preferred configuration is:

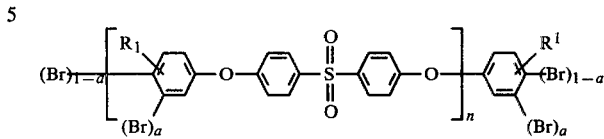

wherein n is 2 or 3 and a and $R^1$ are as previously defined.

The production of such oligomers was unexpected because the reaction to produce such polymers involves a phenoxide displacement of an aryl bromide containing an electron donating group. Heretofore, it was generally believed that only aryl bromides with electron withdrawing groups undergo this type of polymerization. J. B. Rose, "Polymer", 15, p. 456 (1974); R. N. Johnson et al, "J. Poly. Science", Part A-1, 5, p. 2375 (1967).

As will be hereinafter demonstrated, the amount of dibromobenzene relative to the sulfonyldiphenol can be varied to vary the amount of oligomers obtained. A preferred ratio of dibromobenzene to sulfonyldiphenol is a molar ratio in the range of between about 2:1 and about 10:1, preferably between about 3:1 and about 6:1.

Examples of suitable bromophenoxydiphenyl sulfone oligomers include:
1,3-bis-(4-(4-(3-bromophenoxy)benzene sulfonyl)phenoxy)benzene,
1,3-bis-(4-(4-(4-bromophenoxy)benzene sulfonyl)phenoxy)benzene,
1-(4-(4-(3-bromophenoxy)benzene sulfonyl)phenoxy-3-(4-(4-(4-bromophenoxy)benzene sulfonyl)phenoxy)benzene,
1,4-bis-(4-(4-(3-bromophenoxy)benzene sulfonyl)phenoxy)benzene,
1,4-bis-(4-(4-(4-bromophenoxy)benzene sulfonyl)phenoxy)benzene,
1-(4-(4-(3-bromophenoxy)benzene sulfonyl)phenoxy)-4-(4-(4-(4-bromophenoxy)benzene sulfonyl)phenoxy)benzene,
1,3-bis-(4-(4-(3-bromo-5-methylphenoxy)benzenesulfonyl)phenoxy)-5-methyl benzene,
1,4-bis-(4-(4-(4-bromo-2-methylphenoxy)benzenesulfonyl)phenoxy)-2-methyl benzene,
1,3-bis-(4-(4-(3-bromo-2-methylphenoxy)benzenesulfonyl)phenoxy)-2-methyl benzene,
1,3-bis-(4-(4-(4-bromo-2-methylphenoxy)benzenesulfonyl)phenoxy)-5-methyl benzene,
1,3-bis-(4-(4-(4-bromo-2-methylphenoxy)benzenesulfonyl)phenoxy)-2-methyl benzene,
1,4-bis-(4-(4-(3-bromo-5methylphenoxy)benzenesulfonyl)phenoxy)-2-methyl benzene,
1,4-bis-(4-(4-(3-bromo-2-methylphenoxy)benzenesulfonyl)phenoxy)-2-methyl benzene,
1,3-bis-(4-(4-(3-bromo-2-methylphenoxy)benzenesulfonyl)phenoxy)-5-methyl benzene,
1,3-bis-(4-(4-(3-bromo-5-methylphenoxy)benzenesulfonyl)phenoxy)-2-methyl benzene,
1-(4-(4-(3-bromo-5-methylphenoxy)benzene sulfonyl)phenoxy)-3-(4-(4-(3-bromo-2-methylphenoxy)benzene sulfonyl)phenoxy)-5-methyl benzene,
1-(4-(4-(3-bromo-5-methylphenoxy)benzene sulfonyl)phenoxy)-3-(4-(4-(4-bromo-2-methylphenoxy)benzene sulfonyl)phenoxy)-5-methyl benzene, 1-(4-(4-(3-bromo-2-methylphenoxy)benzene sulfonyl)phenoxy)-3-(4-(4-(4-bromo-2-methylphenoxy)benzene sulfonyl)phenoxy)-5-methyl benzene,
1-(4-(4-(3-bromo-5-methylphenoxy)benzene sulfonyl)phenoxy)-3-(4-(4-(3-bromo-2-methylphenoxy)benzene sulfonyl)phenoxy)-2-methyl benzene,
1-(4-(4-(3-bromo-5-methylphenoxy)benzene sulfonyl)phenoxy)-3-(4-(4-(4-bromo-2-methylphenoxy)benzene sulfonyl)phenoxy)-2-methyl benzene,
1-(4-(4-(3-bromo-2-methylphenoxy)benzene sulfonyl)phenoxy)-3-(4-(4-(4-bromo-2-methylphenoxy)benzene sulfonyl)phenoxy)-2-methyl benzene,
1-(4-(4-(3-bromo-5-methylphenoxy)benzene sulfonyl)phenoxy)-4-(4-(4-(3-bromo-2-methylphenoxy)benzene sulfonyl)phenoxy)-2-methyl benzene,
1-(4-(4-(3-bromo-5-methylphenoxy)benzene sulfonyl)phenoxy)-4-(4-(4-(4-bromo-2-methylphenoxy)benzene sulfonyl)phenoxy)-2-methyl benzene,
1-(4-(4-(3-bromo-2-methylphenoxy)benzene sulfonyl)phenoxy)-4-(4-(4-(4-bromo-2-methylphenoxy)benzene sulfonyl)phenoxy)-2-methyl benzene,
4,4'-bis-(3-(4-(4-(3-bromophenoxy)benzene sulfonyl)phenoxy)phenoxy)diphenyl sulfone,
4,4'-bis-(4-(4-(4-bromophenoxy)benzene sulfonyl)phenoxy)phenoxy)diphenyl sulfone,
4,4'-bis-(3-(4-(4-(4-bromophenoxy)benzene sulfonyl)phenoxy)phenoxy)diphenyl sulfone,
4,4'-bis-(4-(4-(4-(3-bromophenoxy)benzene sulfonyl)phenoxy)phenoxy)diphenyl sulfone,
4-(3-(4-(4-(3-bromophenoxy)benzene sulfonyl)phenoxy)phenoxy)-4'-(3-(4-(4-(4-bromophenoxy)benzenesulfonyl)phenoxy)phenoxy)diphenyl sulfone,
4-(3-(4-(4-(3-bromophenoxy)benzene sulfonyl)phenoxy)phenoxy)-4'-(4-(4-(4-bromophenoxy)benzenesulfonyl)phenoxy)phenoxy)diphenyl sulfone,
4-(3-(4-(4-(4-bromophenoxy)benzene sulfonyl)phenoxy)phenoxy)-4'-(4-(4-(4-bromophenoxy)benzenesulfonyl)phenoxy)phenoxy)diphenyl sulfone,
4-(4-(4-(4-(3-bromophenoxy)benzene sulfonyl)phenoxy)phenoxy)-4'-(3-(4-(4-(4-bromophenoxy)benzenesulfonyl)phenoxy)phenoxy)diphenyl sulfone,
4-(4-(4-(4-(3-bromophenoxy)benzene sulfonyl)phenoxy)phenoxy)-4'-(3-(4-(4-(3-bromophenoxy)benzenesulfonyl)phenoxy)phenoxy)diphenyl sulfone,
4-(4-(4-(4-(3-bromophenoxy)benzene sulfonyl)phenoxy)phenoxy)-4'-(4-(4-(4-bromophenoxy)benzenesulfonyl)phenoxy)phenoxy)diphenyl sulfone,
1,3-bis-(4-(2-(3-bromophenoxy)benzene sulfonyl)phenoxy)benzene,
1,3-bis-(4-(2-(4-bromophenoxy)benzene sulfonyl)phenoxy)benzene,
1-(4-(2-(3-bromophenoxy)benzene sulfonyl)phenoxy)-3-(4-(2-(4-bromophenoxy)benzene sulfonyl)phenoxy)-benzene,
1,4-bis-(4-(2-(3-bromophenoxy)benzene sulfonyl)phenoxy)benzene,
1,4-bis-(4-(2-(4-bromophenoxy)benzene sulfonyl)phenoxy)benzene,
1-(4-(2-(3-bromophenoxy)benzene sulfonyl)phenoxy)-4-(4-(2-(4-bromophenoxy)benzene sulfonyl)phenoxy)-benzene,
1,3-bis-(4-(4-(3-bromo-5-phenylphenoxy)benzenesulfonyl)phenoxy)-5-phenyl benzene,
1,4-bis-(4-(4-(4-bromo-2-phenylphenoxy)benzenesulfonyl)phenoxy)-2-phenyl benzene,
1,3-bis-(4-(4-(3-bromo-2-phenylphenoxy)benzenesulfonyl)phenoxy)-2-phenyl benzene,
1,3-bis-(4-(4-(4-bromo-2phenylphenoxy)benzenesulfonyl)phenoxy)-5-phenyl benzene,
1,3-bis-(4-(4-(4-bromo-2-phenylphenoxy)benzenesulfonyl)phenoxy)-2-phenyl benzene,
1,4-bis-(4-(4-(3-bromo-5-phenylphenoxy)benzenesulfonyl)phenoxy)-2-phenyl benzene,
1,4-bis-(4-(4-(3-bromo-2-phenylphenoxy)benzenesulfonyl)phenoxy)-2-phenyl benzene,
1,3-bis-(4-(4-(3-bromo-2-phenylphenoxy)benzenesulfonyl)phenoxy)-5-phenyl benzene,
1,3-bis-(4-(4-(3-bromo-5-phenylphenoxy)benzenesulfonyl)phenoxy)-2-phenyl benzene,
1-(4-(4-(3-bromo-5-phenylphenoxy)benzene sulfonyl)phenoxy)-3-(4-(4-(3-bromo-2-phenylphenoxy)benzene sulfonyl)phenoxy)-5-phenyl benzene,
1-(4-(4-(3-bromo-5-phenylphenoxy)benzene sulfonyl)phenoxy)-3-(4-(4-(4-bromo-2-phenylphenoxy)benzene sulfonyl)phenoxy)-5-phenyl benzene,
1-(4-(4-(3-bromo-2-phenylphenoxy)benzene sulfonyl)phenoxy)-3-(4-(4-(4-bromo-2-phenylphenoxy)benzene sulfonyl)phenoxy)-5-phenyl benzene,
1-(4-(4-(3-bromo-5-phenylphenoxy)benzene sulfonyl)phenoxy)-3-(4-(4-(3-bromo-2-phenylphenoxy)benzene sulfonyl)phenoxy)-2-phenyl benzene,
1-(4-(4-(3-bromo-5-phenylphenoxy)benzene sulfonyl)phenoxy)-3-(4-(4-(4-bromo-2-phenylphenoxy)benzene sulfonyl)phenoxy)-2-phenyl benzene,
1-(4-(4-(3-bromo-2-phenylphenoxy)benzene sulfonyl)phenoxy)-3-(4-(4-(4-bromo-2-phenylphenoxy)benzene sulfonyl)phenoxy)-2-phenyl benzene,
1-(4-(4-(3-bromo-5-phenylphenoxy)benzene sulfonyl)phenoxy)-4-(4-(4-(3-bromo-2-phenylphenoxy)benzene sulfonyl)phenoxy)-2-phenyl benzene,
1-(4-(4-(3-bromo-5-phenylphenoxy)benzene sulfonyl)phenoxy)-4-(4-(4-(4-bromo-2-phenylphenoxy)benzene sulfonyl)phenoxy)-2-phenyl benzene,
1-(4-(4-(3-bromo-2-phenylphenoxy)benzene sulfonyl)phenoxy)-4-(4-(4-(4-bromo-2-phenylphenoxy)benzene sulfonyl)phenoxy)-2-phenyl benzene,
4,2'-bis-(3-(4-(4-(3-bromophenoxy)benzene sulfonyl)phenoxy)phenoxy)diphenyl sulfone,
4,2'-bis-(4-(4-(4-bromophenoxy)benzene sulfonyl)phenoxy)phenoxy)diphenyl sulfone,
4,2'-bis-(3-(4-(4-(4-bromophenoxy)benzene sulfonyl)phenoxy)phenoxy)diphenyl sulfone,
4,2'-bis-(4-(4-(4-(3-bromophenoxy)benzene sulfonyl)phenoxy)phenoxy)diphenyl sulfone,
4-(3-(4-(4-(3-bromophenoxy)benzene sulfonyl)phenoxy)phenoxy)-2'-(3-(4-(4-(4-bromophenoxy)benzenesulfonyl)phenoxy)phenoxy)diphenyl sulfone,
4-(3-(4-(4-(3-bromophenoxy)benzene sulfonyl)phenoxy)phenoxy)-2'-(4-(4-(4-bromophenoxy)benzenesulfonyl)phenoxy)phenoxy)diphenyl sulfone,
4-(3-(4-(4-(4-bromophenoxy)benzene sulfonyl)phenoxy)phenoxy)-2'-(4-(4-(4-bromophenoxy)benzenesulfonyl)phenoxy)phenoxy)diphenyl sulfone,
4-(4-(4-(3-bromophenoxy)benzene sulfonyl)phenoxy)phenoxy)-2'-(3-(4-(4-(4-bromophenoxy)benzenesulfonyl)phenoxy)phenoxy)diphenyl sulfone,
4-(4-(4-(4-(3-bromophenoxy)benzene sulfonyl)phenoxy)phenoxy)-2'-(3-(4-(4-(3-bromophenoxy)benzenesulfonyl)phenoxy)phenoxy)diphenyl sulfone,
4-(4-(4-(4-(3-bromophenoxy)benzene sulfonyl)phenoxy)phenoxy)-2'-(4-(4-(4-bromophenoxy)benzenesulfonyl)phenoxy)phenoxy)diphenyl sulfone.

As in the case of the monomeric bis-bromophenoxydiphenyl sulfone, the oligomeric bromophenoxydiphenyl sulfone can be reacted with the same substituted terminal acetylene compounds defined previously as used in Reaction (II) under the same conditions to produce oligomers having the formula:

$$(ZC\equiv C)_{1-a} \begin{bmatrix} R^1 \\ \phantom{x} \\ (ZC\equiv C)_a \end{bmatrix} \!\!-\!\!O\!\!-\!\!\begin{array}{c}O\\ \|\\ S\\ \|\\ O\end{array}\!\!-\!\!O\!\!-\!\!\begin{bmatrix} R^1 \\ \phantom{x} \\ (C\equiv CZ)_a \end{bmatrix}_n (C\equiv CZ)_{1-a}$$

wherein n is 2 or 3 and a, R$^1$ and Z are as previously defined.

Examples of suitable hydroxy-acetylene terminated oligomers include:
1,3-bis-(4-(4-(3-(3-hydroxy-3-methylbutynyl)phenoxy)-benzene sulfonyl)phenoxy)benzene,
1,3-bis-(4-(4-(4-(3-hydroxy-3-methylbutynyl)phenoxy)-benzene sulfonyl)phenoxy)benzene,
1,4-bis-(4-(4-(3-(3-hydroxy-3-methylbutynyl)phenoxy)-benzene sulfonyl)phenoxy)benzene,
1,4-bis-(4-(4-(4-(3-hydroxy-3-methylbutynyl)phenoxy)-benzene sulfonyl)phenoxy)benzene,
1-(4-(4-(3-(3-hydroxy-3-methylbutynyl)phenoxy)benzenesulfonyl)phenoxy)-3-(4-(4-(4-(3-hydroxy-3-methylbutynyl)phenoxy)benzene sulfonyl)phenoxy)-benzene,
1-(4-(4-(3-(3-hydroxy-3-methylbutynyl)phenoxy)benzenesulfonyl)phenoxy)-4-(4-(4-(4-(3-hydroxy-3-methylbutynyl)phenoxy)benzene sulfonyl)phenoxy)-benzene,
1,3-bis-(4-(4-(3-(3-hydroxy-3-ethylpentynyl)phenoxy)-benzene sulfonyl)phenoxy)benzene,
1,3-bis-(4-(4-(4-(3-hydroxy-3-ethylpentynyl)phenoxy)-benzene sulfonyl)phenoxy)benzene,
1,4-bis-(4-(4-(3-(3-hydroxy-3-ethylpentynyl)phenoxy)-benzene sulfonyl)phenoxy)benzene,
1,4-bis-(4-(4-(4-(3-hydroxy-3-ethylpentynyl)phenoxy)-benzene sulfonyl)phenoxy)benzene,
1-(4-(4-(3-(3-hydroxy-3-ethylpentynyl)phenoxy)benzenesulfonyl)phenoxy)-3-(4-(4-(4-(3-hydroxy-3-ethylpentynyl)phenoxy)benzene sulfonyl)phenoxy)benzene,
1-(4-(4-(3-(3-hydroxy-3-ethylpentynyl)phenoxy)benzenesulfonyl)phenoxy)-4-(4-(4-(4-(3-hydroxy-3-ethylpentynyl)phenoxy)benzene sulfonyl)phenoxy)benzene,
1,3-bis-(4-(4-(3-(2-(1-hydroxycyclohexyl)ethynyl)-phenoxy)benzene sulfonyl)phenoxy)benzene,
1,3-bis-(4-(4-(4-(2-(1-hydroxycyclohexyl)ethynyl)-phenoxy)benzene sulfonyl)phenoxy)benzene,
1,4-bis-(4-(4-(3-(2-(1-hydroxycyclohexyl)ethynyl)-phenoxy)benzene sulfonyl)phenoxy)benzene,
1,4-bis-(4-(4-(4-(2-(1-hydroxycyclohexyl)ethynyl)-phenoxy)benzene sulfonyl)phenoxy)benzene,
1-(4-(4-(3-(2-(1-hydroxycyclohexyl)ethynyl)phenoxy)-benzene sulfonyl)phenoxy)-3-(4-(4-(4-(2-(1-hydroxycyclohexyl)ethynyl)phenoxy)benzene sulfonyl)-phenoxy)benzene,
1-(4-(4-(3-(2-(1-hydroxycyclohexyl)ethynyl)phenoxy)-benzene sulfonyl)phenoxy)-4-(4-(4-(4-(2-(1-hydroxycyclohexyl)ethynyl)phenoxy)benzene sulfonyl)-phenoxy)benzene,
4,4'-bis-(3-(4-(4-(3-hydroxy-3-methylbutynyl)-phenoxy)benzene sulfonyl)phenoxy)phenoxy)diphenyl sulfone,
4,4'-bis-(4-(4-(4-(4-(3-hydroxy-3-methylbutynyl)-phenoxy)benzene sulfonyl)phenoxy)phenoxy)diphenyl sulfone,
4,4'-bis-(3-(4-(4-(4-(3-hydroxy-3-methylbutynyl)-phenoxy)benzene sulfonyl)phenoxy)phenoxy)diphenyl sulfone,
4,4'-bis-(4-(4-(3-(3-hydroxy-3-methylbutynyl)-phenoxy)benzene sulfonyl)phenoxy)phenoxy)diphenyl sulfone,
4-(3-(4-(4-(3-(3-hydroxy-3-methylbutynyl)phenoxy)-benzene sulfonyl)phenoxy)phenoxy)-4'-(3-(4-(4-(4-(3-hydroxy-3-methylbutynyl)phenoxy)benzene sulfonyl)phenoxy)phenoxy)diphenyl sulfone,
4-(3-(4-(4-(3-(3-hydroxy-3-methylbutynyl)phenoxy)-benzene sulfonyl)phenoxy)phenoxy)-4'-(4-(4-(4-(3-hydroxy-3-methylbutynyl)phenoxy)benzene sulfonyl)phenoxy)phenoxy)diphenyl sulfone,
4-(3-(4-(4-(3-hydroxy-3-methylbutynyl)phenoxy)-benzene sulfonyl)phenoxy)phenoxy)-4'-(4-(4-(4-(3-hydroxy-3-methylbutynyl)phenoxy)benzenesulfonyl)phenoxy)phenoxy)diphenyl sulfone,
4-(4-(4-(3-(3-hydroxy-3-methylbutynyl)phenoxy)-benzene sulfonyl)phenoxy)phenoxy)-4'-(3-(4-(4-(3-hydroxy-3-methylbutynyl)phenoxy)benzenesulfonyl)phenoxy)phenoxy)diphenyl sulfone,
4-(4-(4-(3-(3-hydroxy-3-methylbutynyl)phenoxy)-benzene sulfonyl)phenoxy)phenoxy)-4'-(3-(4-(4-(3-(3-hydroxy-3-methylbutynyl)phenoxy)benzenesulfonyl)phenoxy)phenoxy)diphenyl sulfone,
4-(4-(4-(3-(3-hydroxy-3-methylbutynyl)phenoxy)-benzene sulfonyl)phenoxy)phenoxy)-4'-(4-(4-(4-(3-hydroxy-3-methylbutynyl)phenoxy)benzene sulfonyl)phenoxy)phenoxy)diphenyl sulfone,
1,3-bis-(4-(2-(3-(3-hydroxy-3-methylbutynyl)phenoxy)-benzene sulfonyl)phenoxy)benzene,
1,3-bis-(4-(2-(4-(3-hydroxy-3-methylbutynyl)phenoxy)-benzene sulfonyl)phenoxy)benzene,
1,4-bis-(4-(2-(3-(3-hydroxy-3-methylbutynyl)phenoxy)-benzene sulfonyl)phenoxy)benzene,
1,4-bis-(4-(2-(4-(3-hydroxy-3-methylbutynyl)phenoxy)-benzene sulfonyl)phenoxy)benzene,
1-(4-(2-(3-(3-hydroxy-3-methylbutynyl)phenoxy)benzene-sulfonyl)phenoxy)-3-(4-(2-(4-(3-hydroxy-3-methylbutynyl)phenoxy)benzene sulfonyl)phenoxy)-benzene,
1-(4-(2-(3-(3-hydroxy-3-methylbutynyl)phenoxy)benzene-sulfonyl)phenoxy)-4-(4-(2-(4-(3-hydroxy-3-methylbutynyl)phenoxy)benzene sulfonyl)phenoxy)-benzene,
1,3-bis-(4-(2-(3-(3-hydroxy-3-ethylpentynyl)phenoxy)-benzene sulfonyl)phenoxy)benzene,
1,3-bis-(4-(2-(4-(3-hydroxy-3-ethylpentynyl)phenoxy)-benzene sulfonyl)phenoxy)benzene,
1,4-bis-(4-(2-(3-(3-hydroxy-3-ethylpentynyl)phenoxy)-benzene sulfonyl)phenoxy)benzene,
1,4-bis-(4-(2-(4-(3-hydroxy-3-ethylpentynyl)phenoxy)-benzene sulfonyl)phenoxy)benzene,
1-(4-(2-(3-(3-hydroxy-3-ethylpentynyl)phenoxy)benzene-sulfonyl)phenoxy)-3-(4-(2-(4-(3-hydroxy-3- ethylpentynyl)phenoxy)benzene sulfonyl)phenoxy)-benzene,
1-(4-(2-(3-(3-hydroxy-3-ethylpentynyl)phenoxy)benzene-sulfonyl)phenoxy)-4-(4-(2-(4-(3-hydroxy-3-ethylpentynyl)phenoxy)benzene sulfonyl)phenoxy)-benzene,
1,3-bis-(4-(2-(3-(2-(1-hydroxycyclohexyl)ethynyl)-phenoxy)benzene sulfonyl)phenoxy)benzene,
1,3-bis-(4-(2-(4-(2-(1-hydroxycyclohexyl)ethynyl)-phenoxy)benzene sulfonyl)phenoxy)benzene,
1,4-bis-(4-(2-(3-(2-(1-hydroxycyclohexyl)ethynyl)-phenoxy)benzene sulfonyl)phenoxy)benzene,
1,4-bis-(4-(2-(4-(2-(1-hydroxycyclohexyl)ethynyl)-phenoxy)benzene sulfonyl)phenoxy)benzene,
1-(4-(2-(3-(2-(1-hydroxycyclohexyl)ethynyl)phenoxy)-benzene sulfonyl)phenoxy)-3-(4-(2-(4-(2-(1-hydroxycyclohexyl)ethynyl)phenoxy)benzene sulfonyl)-phenoxy)benzene,
1-(4-(2-(3-(2-(1-hydroxycyclohexyl)ethynyl)phenoxy)-benzene sulfonyl)phenoxy)-4-(4-(2-(4-(2-(1-hydroxycyclohexyl)ethynyl)phenoxy)benzene sulfonyl)-phenoxy)benzene,
4,2'-bis-(3-(4-(4-(3-(3-hydroxy-3-methylbutynyl)-phenoxy)benzene sulfonyl)phenoxy)phenoxy)diphenyl sulfone,
4,2'-bis-(4-(4-(4-(3-hydroxy-3-methylbutynyl)-phenoxy)benzene sulfonyl)phenoxy)phenoxy)diphenyl sulfone,
4,2'-bis-(3-(4-(4-(4-(3-hydroxy-3-methylbutynyl)-phenoxy)benzene sulfonyl)phenoxy)phenoxy)diphenyl sulfone,
4,2'-bis-(4-(4-(4-(3-(3-hydroxy-3-methylbutynyl)-phenoxy)benzene sulfonyl)phenoxy)phenoxy)diphenyl sulfone,
4-(3-(4-(4-(3-(3-hydroxy-3-methylbutynyl)phenoxy)-benzene sulfonyl)phenoxy)phenoxy)-2'-(3-(4-(4-(4-(3-hydroxy-3-methylbutynyl)phenoxy)benzene sulfonyl)phenoxy)phenoxy)diphenyl sulfone,
4-(3-(4-(4-(3-(3-hydroxy-3-methylbutynyl)phenoxy)-benzene sulfonyl)phenoxy)phenoxy)-2'-(4-(4-(4-(4-(3-hydroxy-3-methylbutynyl)phenoxy)benzene sulfonyl)phenoxy)phenoxy)diphenyl sulfone,
4-(3-(4-(4-(4-(3-hydroxy-3-methylbutynyl)phenoxy)-benzene sulfonyl)phenoxy)phenoxy)-2'-(4-(4-(4-(4-(3-hydroxy-3-methylbutynyl)phenoxy)benzene sulfonyl)phenoxy)phenoxy)diphenyl sulfone,
4-(4-(4-(4-(3-(3-hydroxy-3-methylbutynyl)phenoxy)-benzene sulfonyl)phenoxy)phenoxy)-2'-(3-(4-(4-(3-hydroxy-3-methylbutynyl)phenoxy)benzene sulfonyl)phenoxy)phenoxy)diphenyl sulfone,
4-(4-(4-(4-(3-(3-hydroxy-3-methylbutynyl)phenoxy)-benzene sulfonyl)phenoxy)phenoxy)-2'-(3-(4-(4-(3-hydroxy-3-methylbutynyl)phenoxy)benzene sulfonyl)phenoxy)phenoxy)diphenyl sulfone,
4-(4-(4-(4-(3-(3-hydroxy-3-methylbutynyl)phenoxy)-benzene sulfonyl)phenoxy)phenoxy)-2'-(4-(4-(4-(4-(3-hydroxy-3-methylbutynyl)phenoxy)benzene sulfonyl)phenoxy)phenoxy)diphenyl sulfone, and the like.

The hydroxy-acetylene terminated oligomers can similarly be subjected to base catalyzed cleavage as in Reaction (III) under the same conditions to produce an oligomeric acetylene terminated sulfone having the following structure:

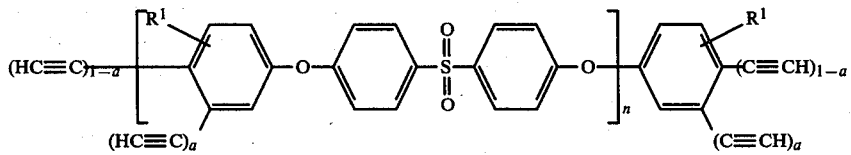

wherein n is 2 or 3 and a and $R^1$ are as previously defined.

Especially preferred are the oligomeric acetylene terminated sulfones having the formula:

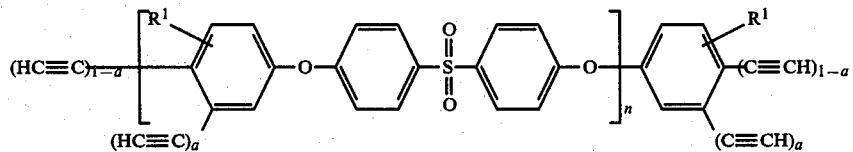

wherein n is 2 or 3 and a and $R^1$ are as previously defined.

Examples of suitable oligomeric acetylene terminated sulfones include:
1,3-bis-(4-(4-(3-ethynylphenoxy)benzene sulfonyl)-phenoxy)benzene,
1,3-bis-(4-(4-(4-ethynylphenoxy)benzene sulfonyl)-phenoxy)benzene,
1,4-bis-(4-(4-(3-ethynylphenoxy)benzene sulfonyl)-phenoxy)benzene,
1,4-bis-(4-(4-(4-ethynylphenoxy)benzene sulfonyl)-phenoxy)benzene,
1-(4-(4-(3-ethynylphenoxy)benzene sulfonyl)phenoxy)-3-(4-(4-(4-ethynylphenoxy)benzene sulfonyl)phenoxy)benzene,
1-(4-(4-(3-ethynylphenoxy)benzene sulfonyl)phenoxy)-4-(4-(4-(4-ethynylphenoxy)benzene sulfonyl)phenoxy)benzene,
4,4'-bis-(3-(4-(4-(3-ethynylphenoxy)benzene sulfonyl)phenoxy)phenoxy)diphenyl sulfone,
4,4'-bis-(4-(4-(4-(4-ethynylphenoxy)benzene sulfonyl)phenoxy)phenoxy)diphenyl sulfone,
4,4'-bis-(3-(4-(4-(4-ethynylphenoxy)benzene sulfonyl)phenoxy)phenoxy)diphenyl sulfone,
4,4'-bis-(4-(4-(3-ethynylphenoxy)benzene sulfonyl)phenoxy)phenoxy)diphenyl sulfone,
4-(3-(4-(4-(3-ethynylphenoxy)benzene sulfonyl)phenoxy)phenoxy)-4'-(3-(4-(4-(4-ethynylphenoxy)benzene sulfonyl)phenoxy)phenoxy)diphenyl sulfone,
4-(3-(4-(4-(3-ethynylphenoxy)benzene sulfonyl)phenoxy)phenoxy)-4'-(4-(4-(4-(4-ethynylphenoxy)benzene sulfonyl)phenoxy)phenoxy)diphenyl sulfone,
4-(3-(4-(4-(4-ethynylphenoxy)benzene sulfonyl)phenoxy)phenoxy)-4'-(4-(4-(4-(4-ethynylphenoxy)benzene sulfonyl)phenoxy)phenoxy)diphenyl sulfone, 4-(4-(4-(4-(3-ethynylphenoxy)benzene sulfonyl)phenoxy)phenoxy)-4'-(3-(4-(4-(4-ethynylphenoxy)benzene sulfonyl)phenoxy)phenoxy)diphenyl sulfone, 4-(4-(4-(4-(3-ethynylphenoxy)benzene sulfonyl)phenoxy)phenoxy)-4'-(3-(4-(4-(3-ethynylphenoxy)benzene sulfonyl)phenoxy)phenoxy)diphenyl sulfone,
4-(4-(4-(4-(3-ethynylphenoxy)benzene sulfonyl)phenoxy)phenoxy)-4'-(4-(4-(4-(4-ethynylphenoxy)benzene sulfonyl)phenoxy)phenoxy)diphenyl sulfone,
1,3-bis-(4-(2-(3-ethynylphenoxy)benzene sulfonyl)phenoxy)benzene,
1,3-bis-(4-(2-(4-ethynylphenoxy)benzene sulfonyl)phenoxy)benzene,
1,4-bis-(4-(2-(3-ethynylphenoxy)benzene sulfonyl)phenoxy)benzene,
1,4-bis-(4-(2-(4-ethynylphenoxy)benzene sulfonyl)phenoxy)benzene,
1-(4-(2-(3-ethynylphenoxy)benzene sulfonyl)phenoxy)-3-(4-(2-(4-ethynylphenoxy)benzene sulfonyl)phenoxy)benzene,
1-(4-(2-(3-ethynylphenoxy)benzene sulfonyl)phenoxy)-4-(4-(2-(4-ethynylphenoxy)benzene sulfonyl)phenoxy)benzene,
4,2'-bis-(3-(4-(4-(3-ethynylphenoxy)benzene sulfonyl)phenoxy)phenoxy)diphenyl sulfone,
4,2'-bis-(4-(4-(4-(4-ethynylphenoxy)benzene sulfonyl)phenoxy)phenoxy)diphenyl sulfone,
4,2'-bis-(3-(4-(4-(4-ethynylphenoxy)benzene sulfonyl)phenoxy)phenoxy)diphenyl sulfone,
4,2'-bis-(4-(4-(4-(3-ethynylphenoxy)benzene sulfonyl)phenoxy)phenoxy)diphenyl sulfone,
4-(3-(4-(4-(3-ethynylphenoxy)benzene sulfonyl)phenoxy)phenoxy)-2'-(3-(4-(4-(4-ethynylphenoxy)benzene sulfonyl)phenoxy)phenoxy)diphenyl sulfone,
4-(3-(4-(4-(3-ethynylphenoxy)benzene sulfonyl)phenoxy)phenoxy)-2'-(4-(4-(4-(4-ethynylphenoxy)benzene sulfonyl)phenoxy)phenoxy)diphenyl sulfone,
4-(3-(4-(4-(4-ethynylphenoxy)benzene sulfonyl)phenoxy)phenoxy)-2'-(4-(4-(4-(4-ethynylphenoxy)benzene sulfonyl)phenoxy)phenoxy)diphenyl sulfone,
4-(4-(4-(3-ethynylphenoxy)benzenne sulfonyl)phenoxy)phenoxy)-2'-(3-(4-(4-(4-ethynylphenoxy)benzene sulfonyl)phenoxy)phenoxy)diphenyl sulfone,
4-(4-(4-(4-(3-ethynylphenoxy)benzene sulfonyl)phenoxy)phenoxy)-2'-(3-(4-(4-(3-ethynylphenoxy)benzene sulfonyl)phenoxy)phenoxy)diphenyl sulfone, and
4-(4-(4-(4-(3-ethynylphenoxy)benzene sulfonyl)phenoxy)phenoxy)-2'-(4-(4-(4-(4-ethynylphenoxy)benzene sulfonyl)phenoxy)phenoxy)diphenyl sulfone, and the like.

According to another embodiment of the present invention, a reaction using the sulfonyldiphenol and meta- or para-dibromobenzene reactants and the conditions of Reaction (I) is conducted with a sodium base, such as sodium hydroxide, sodium carbonate, sodium tertiary butoxide, etc. rather than a potassium base, to produce the following hydroxyphenylbromophenoxyphenyl sulfone:

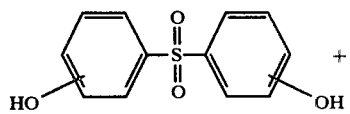

(IV)

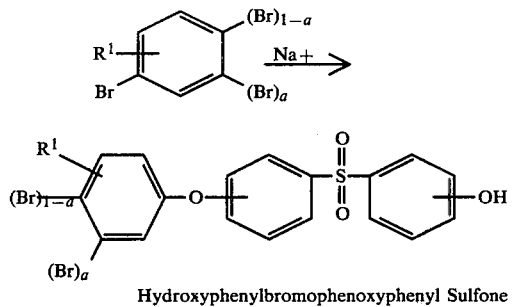

Hydroxyphenylbromophenoxyphenyl Sulfone wherein a and $R^1$ are as previously defined.

Especially preferred is the hydroxyphenylbromophenoxyphenyl sulfone having the formula:

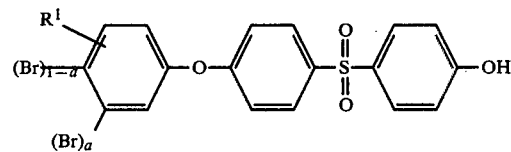

wherein a and $R^1$ are as previously defined.

Suitable hydroxyphenylbromophenoxyphenyl sulfones include:
4-(3-bromophenoxy)-4'-hydroxy diphenyl sulfone,
4-(4-bromophenoxy)-4'-hydroxy diphenyl sulfone,
4-(3-bromo-2-methylphenoxy)-4'-hydroxy diphenyl sulfone,
4-(4-bromo-2-methylphenoxy)-4'-hydroxy diphenyl sulfone,
4-(3-bromo-5-methylphenoxy)-4'-hydroxy diphenyl sulfone,
4-(3-bromophenoxy)-2'-hydroxy diphenyl sulfone,
4-(4-bromophenoxy)-2'-hydroxy diphenyl sulfone,
4-(3-bromo-2-methylphenoxy)-2'-hydroxy diphenyl sulfone,
4-(4-bromo-2-methylphenoxy)-2'-hydroxy diphenyl sulfone,
4-(3-bromo-5-methylphenoxy)-2'-hydroxy diphenyl sulfone,
2-(3-bromophenoxy)-4'-hydroxy diphenyl sulfone,
2-(4-bromophenoxy)-4'-hydroxy diphenyl sulfone,
4-(3-bromo-2-phenylphenoxy)-4'-hydroxy diphenyl sulfone,
4-(4-bromo-2-phenylphenoxy)-4'-hydroxy diphenyl sulfone,
4-(3-bromo-5-phenylphenoxy)-4'-hydroxy diphenyl sulfone.

The half product, hydroxyphenylbromophenoxyphenyl sulfone, can be reacted with a substituted terminal acetylene compound of the type defined above and under the conditions of Reaction (II) to form the corresponding hydroxyacetylenephenoxydiphenyl sulfone having the formula:

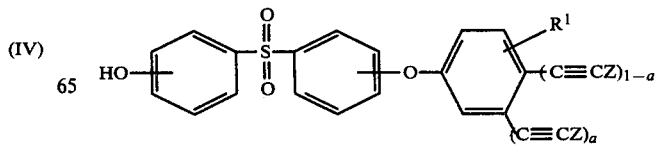

wherein a, $R^1$ and Z are as previously defined.

Especially preferred is the hydroxyacetylenephenoxydiphenyl sulfone having the formula:

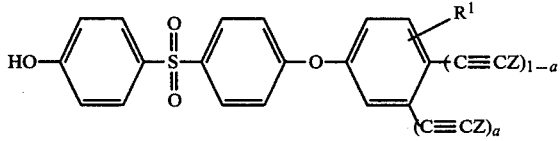

wherein a, $R^1$ and Z are as previously defined.

Examples of suitable hydroxyacetylenephenoxydiphenyl sulfones include:

4-(3-(3-hydroxy-3-methylbutynyl)phenoxy)-4'-hydroxy diphenyl sulfone,
4-(4-(3-hydroxy-3-methylbutynyl)phenoxy)-4'-hydroxy diphenyl sulfone,
4-(3-(3-hydroxy-3-methylbutynyl)-2-methylphenoxy)-4'-hydroxy diphenyl sulfone,
4-(4-(3-hydroxy-3-methylbutynyl)-2-methylphenoxy)-4'-hydroxy diphenyl sulfone,
4-(3-(3-hydroxy-3-methylbutynyl)-5-methylphenoxy)-4'-hydroxy diphenyl sulfone,
4-(3-(3-hydroxy-3-ethylpentynyl)phenoxy)-4'-hydroxy diphenyl sulfone,
4-(4-(3-hydroxy-3-ethylpentynyl)phenoxy)-4'-hydroxy diphenyl sulfone,
4-(3-(3-hydroxy-3-ethylpentynyl)-2-methylphenoxy)-4'-hydroxydiphenyl sulfone,
4-(4-(3-hydroxy-3-ethylpentynyl)-2-methylphenoxy)-4'-hydroxydiphenyl sulfone,
4-(3-(3-hydroxy-3-ethylpentynyl)-5-methylphenoxy)-4'-hydroxydiphenyl sulfone,
4-(3-(2-(1-hydroxycyclohexyl)ethynyl)phenoxy)-4'-hydroxy diphenyl sulfone,
4-(4-(2-(1-hydroxycyclohexyl)ethynyl)phenoxy)-4'-hydroxy diphenyl sulfone,
4-(3-(2-(1-hydroxycyclohexyl)ethynyl)-2-methylphenoxy)-4'-hydroxy diphenyl sulfone,
4-(4-(2-(1-hydroxycyclohexyl)ethynyl)-2-methylphenoxy)-4'-hydroxy diphenyl sulfone,
4-(3-(2-(1-hydroxycyclohexyl)ethynyl)-5-methylphenoxy)-4'-hydroxy diphenyl sulfone,
4-(3-(3-hydroxy-3-methylbutynyl)phenoxy)-2'-hydroxy diphenyl sulfone,
4-(4-(3-hydroxy-3-methylbutynyl)phenoxy)-2'-hydroxy diphenyl sulfone,
4-(3-(3-hydroxy-3-methylbutynyl)-2-methylphenoxy)-2'-hydroxy diphenyl sulfone,
4-(4-(3-hydroxy-3-methylbutynyl)-2-methylphenoxy)-2'-hydroxy diphenyl sulfone,
4-(3-(3-hydroxy-3-methylbutynyl)-5-methylphenoxy)-2'-hydroxy diphenyl sulfone,
4-(3-(3-hydroxy-3-ethylpentynyl)phenoxy)-2'-hydroxy diphenyl sulfone,
4-(4-(3-hydroxy-3-ethylpentynyl)phenoxy)-2'-hydroxy diphenyl sulfone,
4-(3-(3-hydroxy-3-ethylpentynyl)-2-methylphenoxy)-2'-hydroxydiphenyl sulfone,
4-(4-(3-hydroxy-3-ethylpentynyl)-2-methylphenoxy)-2'-hydroxydiphenyl sulfone,
4-(3-(3-hydroxy-3-ethylpentynyl)-5-methylphenoxy)-2'-hydroxydiphenyl sulfone,
4-(3-(2-(1-hydroxycyclohexyl)ethynyl)phenoxy)-2'-hydroxy diphenyl sulfone,
4-(4-(2-(1-hydroxycyclohexyl)ethynyl)phenoxy)-2'-hydroxy diphenyl sulfone,
4-(3-(2-(1-hydroxycyclohexyl)ethynyl)-2-methylphenoxy)-2'-hydroxy diphenyl sulfone,
4-(4-(2-(1-hydroxycyclohexyl)ethynyl)-2-methylphenoxy)-2'-hydroxy diphenyl sulfone,
4-(3-(2-(1-hydroxycyclohexyl)ethynyl)-5-methylphenoxy)-2'-hydroxy diphenyl sulfone.

The resulting acetylene product can then be subjected to base catalyzed cleavage to form an acetylene derivative having the following formula:

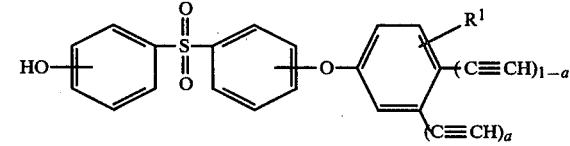

wherein a and $R^1$ are as previously defined.

Especially preferred hydroxy-arylacetylene terminated sulfones are those having the structural formula:

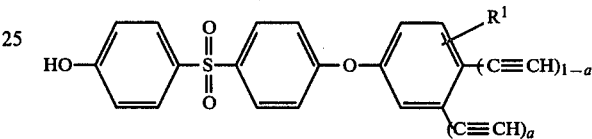

wherein a and $R^1$ are as previously defined.

Suitable hydroxy-arylacetylene terminated sulfones include:

4-(3-ethynylphenoxy)-4'-hydroxy diphenyl sulfone,
4-(4-ethynylphenoxy)-4'-hydroxy diphenyl sulfone,
4-(3-ethynyl-2-methylphenoxy)-4'-hydroxy diphenyl sulfone,
4-(4-ethynyl-2-methylphenoxy)-4'-hydroxy diphenyl sulfone,
4-(3-ethynyl-5-methylphenoxy)-4'-hydroxy diphenyl sulfone,
2-(3-ethynylphenoxy)-4'-hydroxy diphenyl sulfone,
2-(4-ethynylphenoxy)-4'-hydroxy diphenyl sulfone,
4-(3-ethynyl-2-phenylphenoxy)-4'-hydroxy diphenyl sulfone,
4-(4-ethynyl-2-phenylphenoxy)-4'-hydroxy diphenyl sulfone,
4-(3-ethynyl-5-phenylphenoxy)-4'-hydroxy diphenyl sulfone,
4-(3-ethynylphenoxy)-2'-hydroxy diphenyl sulfone,
4-(4-ethynylphenoxy)-2'-hydroxy diphenyl sulfone,
4-(3-ethynyl-2-methylphenoxy)-2'-hydroxy diphenyl sulfone,
4-(4-ethynyl-2-methylphenoxy)-2'-hydroxy diphenyl sulfone,
4-(3-ethynyl-5-methylphenoxy)-2'-hydroxy diphenyl sulfone.

The present hydroxy-arylacetylene terminated sulfones have a variety of uses. For example, such compounds can be used as intermediates in the preparation of diamino-acetylene terminated sulfones which are useful in the preparation of thermosetting acetylene-terminated polyphenylquinoxaline resin. The diamino-acetylene terminated sulfones can be prepared as follows:

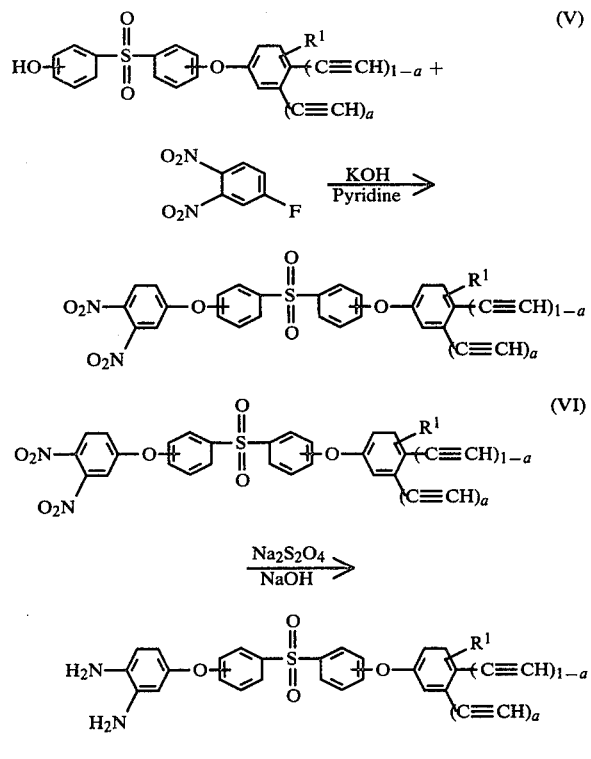

Reaction (V) can be carried out under any suitable temperature and pressure, for example, preferably from about −10° to about +80° C., preferably from about 0° to about 60° C. under atmospheric pressure for a total of about 1 to about 24 hours, preferably from about 2 to about 8 hours. Any suitable base case be used with potassium hydroxide being preferred.

Reaction (VI) can be carried out under any suitable temperature including from about 0° to about 60° C., preferably under ambient temperature (25° C.) and pressure (atmospheric) for a total of from about 1 to about 20 hours, preferably from about 2 to about 8 hours.

Examples of preferred diamino-acetylene terminated sulfones include:
4-(3-bromophenoxy)-4'-(3,4-diaminophenyl)diphenyl sulfone,
4-(4-bromophenoxy)-4'-(3,4-diaminophenoxy)diphenyl sulfone,
4-(3-bromo-2-methylphenoxy)-4'-(3,4-diaminophenoxy)diphenyl sulfone,
4-(4-bromo-2-methylphenoxy)-4'-(3,4-diaminophenoxy)diphenyl sulfone,
4-(3-bromo-5-methylphenoxy)-4'-(3,4-diaminophenoxy)diphenyl sulfone,
4-(3-bromophenoxy)-2'-(3,4-diaminophenoxy)diphenyl sulfone,
4-(4-bromophenoxy)-2'-(3,4-diaminophenoxy)diphenyl sulfone,
4-(3-bromo-2-methylphenoxy)-2'-(3,4-diaminophenoxy)diphenyl sulfone,
4-(4-bromo-2-methylphenoxy)-2'-(3,4-diaminophenoxy)diphenyl sulfone,
4-(3-bromo-5-methylphenoxy)-2'-(3,4-diaminophenoxy)diphenyl sulfone,
2-(3-bromophenoxy)-4'-(3,4-diaminophenoxy)diphenyl sulfone,
2-(4-bromophenoxy)-4'-(3,4-diaminophenoxy)diphenyl sulfone,
4-(3-bromo-2-phenylphenoxy)-4'-(3,4-diaminophenoxy)diphenyl sulfone,
4-(4-bromo-2-phenylphenoxy)-4'-(3,4-diaminophenoxy)diphenyl sulfone,
4-(3-bromo-5-phenylphenoxy)-4'-(3,4-diaminophenoxy)diphenyl sulfone, and the like.

The diamino-acetylene terminated sulfones of the present invention can be used to prepare thermosetting, acetylene-terminated polyphenylquinoxaline resins according to the procedure described by R. F. Kovac et al, "Journal of Polymer Science," Polymer Chemistry Edition, Vol. 15, pp. 1081-95 (1977) for acetylene terminated-terminated quinoxalines (pp. 1090-91), which is hereby incorporated by reference.

According to another aspect of the invention, the hydroxyphenylbromophenoxyphenyl sulfone is reacted with a dibromobenzene, as previously defined, to produce bis-bromophenoxydiphenyl sulfone under the conditions for Reaction (I). The bis-bromophenoxydiphenyl sulfone is formed according to the following reaction:

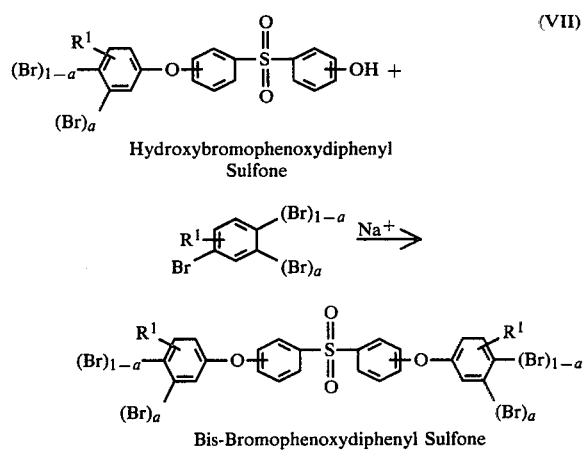

wherein a and $R^1$ are as previously defined.

Especially preferred is the bis-bromophenoxydiphenyl sulfone having the structural formula:

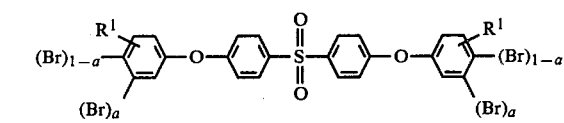

wherein a and $R^1$ are as previously defined.

The bis-bromophenoxydiphenyl sulfones produced in Reaction VII are the same as those produced in Reaction (I) as previously described.

Preferably, the dibromobenzene utilized in Reaction VII is para-dibromobenzene, which may be reacted with a hydroxyphenylbromophenoxylphenyl sulfone in which both the bromine and the hydroxy moieties attached to the same phenyl nucleus are meta, to produce meta, para-bis-bromophenoxydiphenyl sulfone, i.e., wherein the bromine and oxygen moieties attached to the same phenyl nucleus on one side of the bis-bromophenoxydiphenyl sulfone is meta and the bromine and oxygen moieties attached to the same phenyl nucleus on the opposite side of the bis-bromophenoxydiphenyl sulfone are para. Such a meta, para-bis-bromophenoxydiphenyl sulfone can be used to produce an acetylene terminated sulfone wherein the resulting meta-, para-acetylene terminated sulfone has properties even better than those achieved using the acetylene terminated sulfones plus oligomers of the present invention.

This bis-bromophenoxydiphenyl sulfone produced according to Reaction VII can be thereafter reacted with a substituted terminal acetylene compound as previously defined to produce an hydroxy-acetylene terminated sulfone, which can be converted by base catalyzed cleavage to the corresponding acetylene terminated sulfone in the manner and under the conditions previously described.

According to still another embodiment of the present invention, the hydroxyphenylbromophenoxyphenyl sulfone can be reacted with bis-bromophenoxydiphenyl sulfone to form an oligomer according to the following reaction:

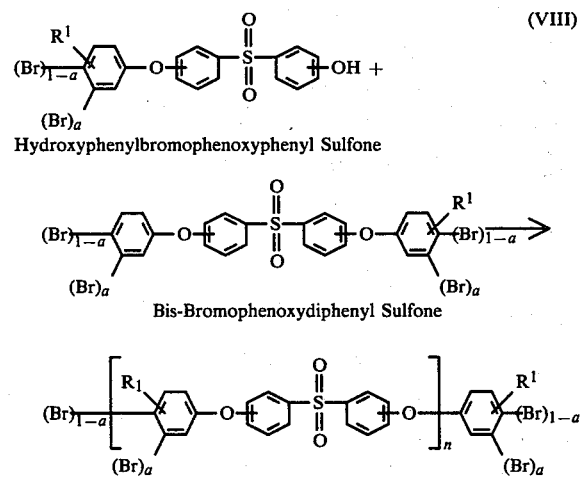

wherein n is 2 or 3 and a and $R^1$ are as previously defined.

Especially preferred bromophenoxydiphenyl sulfone oligomers are those having the formula:

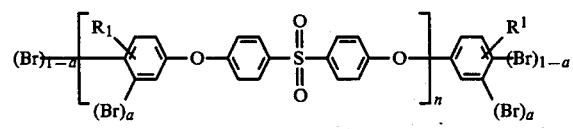

wherein n is 2 or 3 and a and $R^1$ are as previously defined.

Examples of preferred bromophenoxydiphenyl sulfone oligomers produced by Reaction (VIII) are the same as described previously in connection with such oligomers as result from Reaction (I). Reaction (VIII) is conducted under the same conditions as Reaction (I).

The resulting bromophenoxydiphenyl sulfone oligomer can be reacted with a substituted terminal acetylene compound as previously described and thereafter subjected to base catalyzed cleavage to produce an oligomeric acetylene terminated sulfone valuable in the prevention of crystallization of acetylene terminated sulfone during fabrication.

According to another embodiment of the invention, metal contaminants, such as palladium, copper or the like catalytic metals, are removed from a polymerizable acetylenic material, such as monomeric or oligomeric aromatic acetylenes, which process comprises admixing a solution containing the metal-contaminated polymerizable material with an aqueous hydrogen halide, e.g., hydrochloric acid, hydrobromic acid, or the like, and then treating the mixture with water to remove excess hydrogen halide. Next, the admixture is contacted with an amino compound, such as ammonia in the form of ammonium hydroxide, polyamines, such as ethylenediamine, ethylenetriamine, or the like, to form a complex with the metal contaminant which can be separated from the polymerizable acetylenic compound by washing the solution with water. The level of palladium can be reduced to below 20 ppm and that of copper to below 2 ppm using the process of the present invention.

It is important to remove the palladium and copper contaminants from the reaction mixture containing the hydroxy-acetylene terminated sulfone prior to base catalyzed cleavage of the hydroxy-acetylene terminated sulfone, since the metals will catalyze polymerization of the polymerizable acetylene compounds present, including the oligomers, under the conditions used for the base catalyzed cleavage reaction. However, conventional metals removal techniques, such as the use of silica gel adsorbents, are unsuitable. For example, silica gel cannot be used, since the palladium complex will elute from the adsorption column with the acetylenic oligomer. It is essential that the metal contaminants be removed from the acetylene terminated sulfones prior to polymerization of such compounds, since the sulfone would cure at temperatures lower than desired and make it more difficult to fabricate the polymer into the desired form.

The metal contaminated polymerizable material can be contacted with the hydrogen halide under any suitable conditions, preferably ambient temperature and pressure. Similarly, the acid-treated solution can be contacted with the amino compound to form the metal complex under any suitable conditions including a temperature in the range of between about 40° and about 100° C., preferably between about 50° and about 70° C. for a period of about 0.25 to about 2 hours, preferably between about 0.5 to one hour. Atmospheric or super atmospheric pressures can be used as desired. Although ammonia is quite effective for metals removal in accordance with the present invention, the use of ammonium hydroxide can cause foaming of the solution due to escape of ammonia unless superatmospheric pressure is used. Accordingly, the polyamines, such as ethylenediamine, are preferred for ease of operation.

The invention will be further described with reference to the following experimental work. In all of the experiments to follow, the sulfonyldiphenol utilized in the following examples is 4,4'-sulfonyldiphenol and the dibromobenzene is meta-dibromobenzene unless otherwise indicated.

EXAMPLE 1

This example demonstrates the use of a 95/5 mixture of meta-dibromobenzene and para-dibromobenzene in the preparation of a bis-bromophenoxydiphenyl sulfone mixture.

To a 1-liter, 3-necked flask was added 400 milliliters sulfone and 50 grams sulfonyldiphenol (0.2 mole) under nitrogen. To this was added 22.0 grams potassium hydroxide (86.6% pure) (0.34 mole) and 100 milliliters of a 95/5 mixture of meta-dibromobenzene and para-dibromobenzene, respectively, in toluene. The mixture was heated with stirring to remove the water by toluene azeotrope. After the water was removed, the reaction was cooled to 70° C. then 20 milliliters pyridine and 1.0 gram cuprous chloride was added. The reaction was then heated to 175°–180° C. overnight. The reaction was then cooled and to it was added 750 milliliters water followed by three extractions with 750 milliliters of carbon tetrachloride. The carbon tetrachloride was extracted three times with 750 milliliters potassium hydroxide 10% solution then three times with 750 milliliters of water. The carbon tetrachloride was then dried over anhydrous magnesium sulfate and the solvent removed in vacuo. A total of 165.0 grams of dark oil was recovered. This was then distilled at 15 millimeters Hg (1.95 kPa) to remove the excesd dibromobenzene. The recovered dibromobenzene was analyzed by gas chromatography to give essentially the same ratio of isomers which were used initially, i.e., meta-para=95/5. The residue from dibromobenzene distillation in an amount of 50.6 grams was purified by column chromatography over silica gel to eliminate oligomers using toluene to yield a total of 33.4 grams of bis-bromophenoxydiphenyl sulfone as a mixture of isomers melting at 133°–140° C.

EXAMPLE 2

Preparation of Bromophenoxydiphenyl Sulfone Oligomer Mixture

This examples demonstrates the preparation of a bromophenoxydihenyl sulfone oligomer mixture in the absence of a pyridine solvent.

To a mixture of 800 milliliters of sulfolane and 300 milliliters of toluene, 100 grams sulfonyldiphenol (0.4 mol) was added under nitrogen. Next, 52 grams of potassium hydroxide (87% potassium hydroxide by weight) (0.8 mol) dissolved in 28 milliliters water was added. Then 566 grams meta-dibromobenzene (5% para) (2.4 mol) was added. The mixture was heated with stirring and toluene/water azeotrope was collected. After all the toluene/water had been removed, 45 milliliters water recovered, the mixture was cooled and 2.0 grams cuprous chloride (0.02 mol) was added. This was heated at 160° C.±1° for 16 hours. The reaction mixture was then allowed to cool and to it was added 1 liter of a 10% potassium hydroxide solution.

The mixture was then extracted three times with 500 milliliters of hexane and combined. Slowly a precipitate formed which was filtered to give 11.6 grams almost pure bis-bromophenoxydiphenyl sulfone contaminated with some sulfolane. The aqueous layer was then extracted three times with 500 milliliters of carbon tetrachloride. The 11.6 grams of crystals were dissolved in the carbon tetrachloride and the total was washed three times with 400 milliliters of water. The carbon tetrachloride was dried with anhydrous magnesium sulfate and the carbon tetrachloride removed in vacuo. The residue was triturated with hexane, filtered and dried to a constant weight under vacuum. A total of 106.5 grams was recovered. This material analyzed by gel permeation chromatography was 82.8% bis-bromophenoxydiphenyl sulfone and 17.2% oligomer. The remaining aqueous layer was acidified with concentrated hydrochloric acid to pH 1.5 and then extracted with ether. The ether was washed with water and then dried over anhydrous magnesium sulfate and the ether removed in vacuo. A total of 33.0 grams of unreacted and half reacted sulfonyldiphenol was recovered.

EXAMPLES 3–12

Additional experiments were conducted in which sulfonyldiphenol were reacted with dibromobenzene in sulfolane solvent while varying concentrations, temperature and reaction time following the general procedure of Examples 1 and 2. The results are set forth in Table I below:

TABLE I

| Ex. No. | SDP (mole) | DBB (mole) | DBB/SDP (molar ratio) | CuCl (mole) | Sulfolane (ml.) | Reaction Time (hr.) | Temp. (°C.) | $CCl_4$ Extract (grams) | BPDS/BPDS+ Oligomers (%) | BPDS + Oligomers Yield (Wt. %) |
|---|---|---|---|---|---|---|---|---|---|---|
| 1 | 0.4 | 2.4 | 6/1 | 0.02 | 800 | 16 | $160^a$ | 106.5 | 82.8 | 47 |
| 2 | 0.2 | 0.8 | 4/1 | 0.01 | 400 | 16 | 178–184 | 50.6 | $66^e$ | — |
| 3 | 0.2 | 0.6 | 3/1 | 0.01 | 400 | 16 | $160^a$ | 54.3 | 72.5 | 47 |
| 4 | 0.2 | 1.2 | 6/1 | 0.04 | 400 | 16 | $160^a$ | 75.3 | 80.0 | 68 |
| 5 | 0.2 | 1.21 | 6/1 | 0.01 | 400 | 16 | $141^a$ | 69.5 | 82.5 | 64 |
| 6 | 0.2 | 1.2 | 6/1 | 0.01 | 400 | 16 | $160^a$ | 53.9 | 86.3 | 44 |
| 7 | 0.2 | 1.2 | 6/1 | 0.01 | 400 | 16 | $180^a$ | 52.6 | 83.4 | 47 |
| 8 | 0.4 | 2.4 | 6/1 | 0.02 | 800 | 16 | 120–161 | 93.4 | 93.1 | — |
| 9 | 0.4 | 2.4 | 6/1 | 0.02 | 800 | 5 | 150–156 | 50.7 | 92.9 | — |
| 10 | 0.4 | 2.4 | 6/1 | 0.02 | 800 | 16 | 160–166 | $89.6^f$ | $70^e$ | — |
| 11 | 0.4 | 2.4 | 6/1 | 0.01 | $800^b$ | 16 | 170–187 | 99.2 | $77^e$ | — |
| 12 | 0.4 | 4.0 | 10/1 | 0.02 | 600 | 16 | 133–152 | $0^g$ | — | — |

$^a$Temp. ± 1° C.
$^b$Contained 40 milliliters pyridine
$^c$Contained 20 milliliters pyridine
$^d$Determined by GPC
$^e$Determined by prep. column chromatography
$^f$Portion of material lost due to spillage
$^g$SDP salt crystallized out The results in Table I show that as the ratio of dibromobenzene to sulfonyldiphenol is increased the amount of oligomeric bromophenoxydiphenyl sulfone produced is reduced. Thus, for example, it is seen that in Example 3 the molar ratio of dibromobenzene to sulfonyldiphenol is 3:1 which resulted in 72.5 weight percent bis-bromophenoxydiphenyl sulfone and 27.5 weight percent oligomer. However, when the dibromobenzene/sulfonyldiphenol ratio was increased to 6:1, as in Example 6, this produced 86.3 weight percent bis-bromophenoxydiphenyl sulfone and only 13.7 weight percent oligomer. Thus, if it is desired to increase the amount of oligomer produced in order to avoid crystallization and maintain the resulting acetylene terminated sulfone in a fluid condition, this can be accomplished by using less dibromobenzene.

The effect of temperature and of increasing the amount of copper catalyst upon yield of bis-bromophenoxydiphenyl sulfone plus oligomers is reported in Table I. The yield of bis-bromophenoxydiphenyl sulfone plus oligomers increases from 47% to 64% as the temperature is lowered from 180° C. to 140° C. The ratio bis-bromophenoxydiphenyl sulfone/bis-bromophenoxydiphenyl sulfone plus oligomers stayed about the same. When the ratio of copper was increased, the yield of bis-bromophenoxydiphenyl sulfone plus oligomers increased to 68%. The bis-bromophenoxydiphenyl sulfone/bis-bromophenoxydiphenyl sulfone plus oligomers again remained about the same.

EXAMPLE 13

Preparation of Butynol

To a 3-necked flask, 50 milliliters flash under nitrogen was added 20 milliliters toluene, 5.6 grams 4,4'-bis-(3-bromophenoxy)diphenyl sulfone (10 mmol), and 2.0 grams 2-methyl-3-butyn-2-ol (23 mmol). Then, 0.05 gram cuprous iodide, 0.05 gram bis(triphenylphosphine) palladium dichloride and 0.1 gram triphenylphosphine was added. Finally, 10 milliliters triethylamine was added and the reaction heated to reflux. After five hours, the reaction was cooled and filtered to remove the triethylammonium bromide (3.97 grams recovered). The solvent was removed in vacuo. A total of 9.6 grams of crude product, approximately 70% pure hydroxymethylbutynylphenoxydiphenyl sulfone, was recovered having the formula:

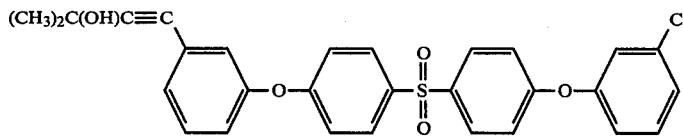

EXAMPLE 14

Preparation of Acetylene Terminated Sulfone

Five grams of 70% by weight of the butynol that was produced in Example 13 was dissolved in 50 milliliters of toluene and to this was added one potassium hydroxide pellet which had been crushed. Using a dean stark trap, 20 milliliters of toluene/acetone were removed in two hours. The crude product was then filtered through alumina and then the solvent was removed in vacuo. Purification through a column of alumina, using toluene, yielded 1.78 grams of acetylene terminated sulfone as a dark yellow oil. The yield was 64 weight percent acetylene terminated sulfone having the formula:

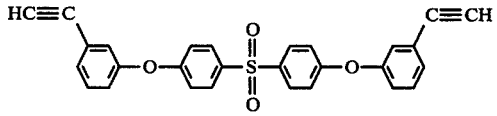

EXAMPLE 15

Preparation of 4-hydroxy-4-(3-bromophenoxy)diphenyl sulfone

To 16 milliliters dimethylsulfoxide (DMSO) under nitrogen was added 2.5 grams sulfonyldiphenol (0.01 mol). To this, at 38° C., was added 4.6 milliliters sodium methoxide solution (25% in methanol) (0.02 mol). The mixture was heated to 120° C. and 3.0 milliliters methanol was distilled. To this was added 10 milliliters pyridine and the temperature was increased to 145° C. removing an additional 2.5 milliliters methanol and 4.5 milliliters pyridine. Then 0.10 grams cuprous chloride (1 mmol) and 9.4 grams meta-dibromobenzene (0.04 mol) was added and the mixture heated to 150° C. for 6 hours. Then 100 milliliters 10% hydrochloric acid was added and the product extracted into ether. The ether was extracted with 10% potassium hydroxide, and the potassium hydroxide was acidified and extracted with ether. The ether was removed in vacuo to yield 5.0 grams of crude material which was purified on a column of silica gel using chloroform as solvent to yield 4-hydroxy-4-(3-bromophenoxy)diphenyl sulfone.

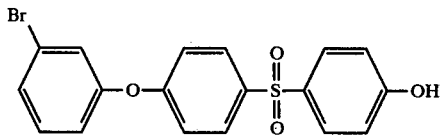

EXAMPLE 16

Preparation of Oligomers by Reacting Bromophenoxydiphenyl Sulfone and Hydroxybromophenoxydiphenyl Sulfone To a 250-milliliter 3-necked flask equipped with a magnetic stirrer, thermometer and distilling head was added 8.3 grams (20 mmol) of the 4-hydroxy-4-(3-bromophenoxy)diphenyl sulfone, 100 milliliters sulfolane, 100 milliliters toluene, 11.2 grams (20 mmol) 4,4'-bis-(3-bromophenoxy)diphenyl sulfone and 1.3 grams (20 mmol) potassium hydroxide under nitrogen. The mixture was heated to remove the water/toluene azeotrope and then 0.1 gram cuprous chloride was added. The reaction was heated at 160° C. for 16 hours then cooled. To this was added 10% potassium hydroxide (200 milliliters) and the mixture was extracted with carbon tetrachloride. The carbon tetrachloride was dried over anhydrous magnesium sulfate then removed in vacuo. Purification on alumina using toluene yielded 8.0 grams bromophenoxydiphenyl sulfone; with methylene chloride yielded 3.6 grams (20%) of the oligomer having the structure below wherein n=2; and with ethyl acetate yielded 2.5 grams (21%) of the following oligomer wherein n=3:

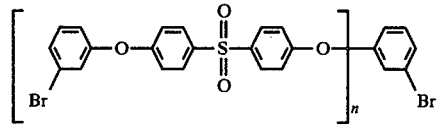

EXAMPLE 17

Preparation of 4-hydroxy-4-(3-bromophenoxy)diphenyl sulfone

To a 5-liter 3-necked flask equipped with a distillation head, nitrogen inlet-outlet, mechanical stirrer and a thermometer were added 1950 milliliters dimethyl sulfoxide (dried over molecular sieves), 375 grams sulfonyldiphenol and 690 milliliters of 25% sodium methoxide in methanol. The mixture was heated for 2 hours under nitrogen (pot temp. 124° C.) collecting overhead at 66° C. After cooling below 100° C., 150 milliliters pyridine was added and the reaction mixture was heated to reflux, collecting fractions and checking for methanol in the overhead by gas liquid chromatography. When methanol no longer came overhead, the reaction was cooled and 15 grams of cuprous chloride and 1425 grams of meta-dibromobenzene were added. The mixture was heated to 150° C. for 6 hours (nitrogen atmosphere). The mixture was cooled and 3 liters of 10% hydrochloric acid was added and the solution extracted twice with one liter of ether. The ether was extracted twice with one liter of 10% potassium hydroxide. The ether layer was dried over anhydrous magnesium sulfate and stripped to give 1101.7 grams crude recovered dibromobenzene. The potassium hydroxide extracts were acidified with hydrochloric acid to pH 1 and extracted twice with one liter of ether. The extracts were dried and stripped to yield 515 grams crude product and 1000 milliliters of methylene chloride were added and the mixture brought to reflux. Upon standing overnight, 12 grams of sulfonyldiphenol crystallized. Stripping the solvent first on a rotary evaporator and finally at high vacuum yielded 471 grams of 4-hydroxy-4-(3-bromophenoxy)diphenyl sulfone.

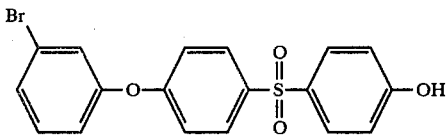

EXAMPLE 18

Preparation of Meta-, Para-Bromophenoxydiphenyl Sulfone Using Para-Dibromobenzene.

The 4-hydroxy-4-(3-bromophenoxy)diphenyl sulfone prepared in Example 17 in the amount of 471 grams in 3 liters of sulfolane was charged to a 12-liter round bottomed flask equipped with a mechanical stirrer, nitrogen inlet-outlet, a dean stark trap, thermometer and condenser along with 74.8 grams potassium hydroxide (87% assay) in 100 milliliters water and 350 milliliters toluene. The water was azeotroped from the mixture. Toluene was then distilled out and the mixture allowed to cool overnight. Next, 823 grams of para-dibromobenzene and 10 grams of cuprous chloride were added and the temperature brought to 160° C. and held for 6 hours. After cooling, 2 liters of 10% aqueous potassium hydroxide were added and the mixture stirred for 20 minutes. After dilution with 3 liters of water, the mixture was extracted three times with one liter of carbon tetrachloride. The organic layers were washed once with one liter of 10% hydrochloric acid and washed twice with one liter of water, dried over anhydrous magnesium sulfate and stripped. Unreacted para-dibromobenzene was removed by extraction with hot hexane to yield 322 grams of crude product. The aqueous portion was acidified with hydrochloric acid and extracted three times with one liter of ethyl acetate. The extracts were washed three times with one liter of water, dried over anhydrous magnesium sulfate and stripped. Sulfolane was distilled from the residue at one millimeter Hg. (0.13 kPa) to yield 188 grams recovered 4-hydroxy-4-(3-bromophenoxy)diphenyl sulfone. Analysis by gas chromatography showed that the the crude product contained 184 grams of meta-, parabromophenoxydiphenyl sufone. The crude product was dissolved in toluene and passed through 115 grams of 80–200 mesh alumina in a standard 2 liter burrette. Elution with toluene produced 132 grams of pure 4-(4-bromophenoxy)-4'(3-bromophenoxy)diphenyl sulfone as a viscous, colorless oil having the formula:

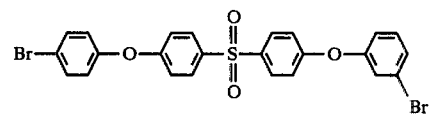

EXAMPLE 19

Preparation of Meta-, Para-Acetylene Terminated Sulfone

One hundred thirty grams of 4-(3-bromophenoxy)4'-(4-bromophenoxy)diphenyl sulfone, as prepared in Example 18, was charged under nitrogen along with 1200 milliliters triethylamine, 0.25 gram triphenylphosphine, 50 grams 2-methyl-3-butyn-2-ol, 0.2 gram bis(triphenylphosphine) palladium dichloride and 0.2 gram cuprous iodide. The reaction was allowed to reflux 16 hours. The amine salt was filtered and the triethylamine stripped. The residue was taken up in 3 liters of toluene and twice washed with 500 milliliters of 5% hydrochloric acid and twice washed with 500 milliliters of water. An aliquot was taken, stripped to give a heavy oil which was placed on 50 milliliters silica gel. Elution with ethylacetate yielded a pale yellow oil which solidified under vacuum to a white solid, mp 66°–68° C.

The remaining toluene solution was refluxed in the presence of 10 grams of sodium hydroxide pellets, and acetone was removed as it formed. When the cleavage was complete, the hot solution was filtered through a layer of celite, cooled to room temperature and eluted through 500 grams of silica gel. The column was washed with 2 liters of toluene. Stripping the solvent yielded 76.9 grams (74%) of meta-, para-acetylene terminated sulfone having the formula:

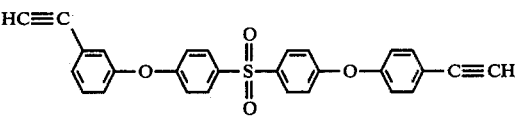

EXAMPLE 20

Preparation of Acetylene Terminated Sulfone

To each of two 12-liter flasks equipped with mechanical stirrers, heating mantles, condensers and nitrogen inlet-outlets were charged 1150 grams of 4,4'-bis-(3-bromophenoxy)diphenyl sulfone, 430 grams 2-methyl-3-butyn-2-ol, 12.5 grams triphenylphosphine and 7.5 liters of triethylamine. The system was purged with nitrogen. Bis(triphenylphosphine)palladium dichloride (2.5 grams) and cuprous iodide (2.5 grams) were added and the temperature raised to reflux with vigorous stirring. The heats were cut back once the reaction started because of the exothermic neutrallization of hydrobromic acid. After about 2.5 hours, the exothermicity was over. Reflux was maintained for 6 hours. The mixture was cooled to room temperature and filtered. Triethylamine was stripped under reduced pressure and the residue from both pots taken up in 6 liters of toluene and combined. The toluene solution was twice washed with one liter of 10% sulfuric acid and one liter of water, respectively, and then washed with one liter of saturated sodium bicarbonate and one liter of water. The organic layer was dried over magnesium sulfate, filtered and charged to a 12 liter pot with 10 grams of sodium hydroxide pellets. The pot was stirred vigorously with a mechanical stirrer and heated to reflux. A toluene-acetone mixture was distilled slowly over a 6 hour period until the acetone content of the overhead was less than one percent. The hot solution was filtered through celite and cooled to room temperature. The dark red colored solution was passed through 6 gallons of 8-14 mesh Fuller's Earth and eluted with an additional 10 gallons of toluene to yield a yellow solution. This was passed through silica gel columns (500 grams in 2 liter burrettes) to remove small amounts of acetylene terminated sulfone oligomers. The eluent was monitored by thin layer chromatography and the column replaced when acetylene terminated sulfone oligomers broke through. A total of 6 kilograms of silica gel was used. Stripping the toluene produced 820 grams, 46%, of acetylene terminated sulfone. Washing the Fuller's Earth with 4 gallons of methylene chloride produced an additional 178 grams of acetylene terminated sulfone which contained 8% acetylene terminated sulfone oligomers by gel permeation chromatography.

EXAMPLE 21

Preparation of Acetylene Terminated Sulfone Oligomers

A mixture containing 17% 4,4'-bis-(3-bromophenoxy)diphenyl sulfone and 83% of the analogous oligomers (1038 grams) was charged along with 1850 milliliters N-methylpyrolidine, 3 liters of triethylamine, 400 grams of methylbutynol, 12.5 grams of triphenylphosphine, 2.5 grams of bis(triphenylphosphine) palladium dichloride and 2.5 grams of cuprous iodide to the apparatus used in the previous example. The reaction was carried out as above. The crude acetylene terminated sulfone oligomer solution after cleavage was passed through one kilogram of Fuller's Earth to remove color and stripped to yield a yellow solid. The material could be ground to a powder, but it usually caked upon standing. Gel permeation chromatography indicates the material is 24% acetylene terminated sulfone and 76% acetylene terminated sulfone oligomers having the following formula where n=2 and 3:

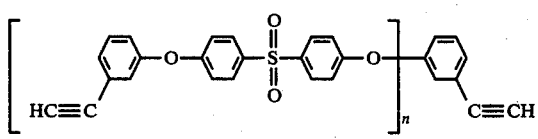

The following example demonstrates use of the metals separation process of the present invention prior to base catalyzed cleavage of the hydroxy acetylene terminated sulfone.

EXAMPLE 22

Preparation of Acetylene Terminated Sulfone-Acetylene Terminated Sulfone Oligomer Mixture A mixture in the amount of 23 grams containing 81% bromophenoxydiphenyl sulfone and 19% of the oligomeric analogs was charged along with 8.6 grams of 2-methyl-3-butyn-2-ol, 150 milliliters triethylamine and 0.25 grams of triphenylphosphine to a 250 milliliter flask equipped with a thermometer, magnetic stirrer, nitrogen inlet-outlet and a condenser. A nitrogen atmosphere was established and 50 milligrams of bis(triphenylphosphine) palladium dichloride and 50 milligrams of cuprous iodide were added. The mixture was brought to reflux for 6 hours. The mixture was filtered and the filtercake washed with a little triethylamine. The filtrate and wash were stripped and the residue taken up in about 300 milliliters of toluene. The solution was washed with 100 milliliters of 15% hydrochloric acid and 100 milliliters of water. Three milliliters of ethylene diamine were added and the solution brought to 60° C. for 30 minutes to complex traces of palladium. The solution was washed thoroughly with water. Analysis by atomic absorption at this point indicates less than 20 ppm palladium on a solvent-free basis. Several pellets of sodium hydroxide were added to the toluene solution, and the mixture was refluxed while removing acetone as it formed. When the formation of acetone ceased, the hot solution was treated with 2 grams of charcoal and filtered through a layer of celite. Stripping the solvent gave 16.8 grams of an orange oil (91%). Gel permeation chromatography indicated 79% acetylene terminated sulfone and 21% acetylene terminated sulfone oligomers.

The following example demonstrates the metals separation process of the present invention for removal of both palladium and copper contaminates prior to base catalyzed cleavage of the hydroxy acetylene terminated sulfone.

EXAMPLE 23

A 50 gallon (190 liters) Pfaudler kettle was charged with 74.5 kilograms of triethylamine, 14.3 kilograms of the bis-bromophenoxydiphenyl sulfone (79% monomer-21% oligomer) produced in Example 22 and prepared according to the procedure of Example 22, 5.4 kilograms of 2-methyl-3-butyn-2-ol, 0.20 kilogram of biphenylphosphine, 39 grams of dichloro-bis-(triphenylphosphine)palladium and 39 grams of cuprous iodide. The mixture was refluxed for 8 hours. After cooling to room temperature, the amine hydrobromide salts were removed by filtration. The filtrate was recharged to the kettle and the triethylamine was distilled under reduced pressure of 150 mg. Hg. The residue was dissolved in 72.6 kilograms of toluene. A mixture of 45.4 liters of water and 24.6 liters of concentrated hydrochloric acid was added. After stirring vigorously, the layers were separated. The organic phase was washed with 68.1 liters of water and the layers separated. Ethylenediamine (3.6 kilograms) was added and the temperature brought to 60° C. and held for ½ hour. The mixture was then washed with 68.1 liters of water four times until the washes were neutral. The temperature was maintained at 60° C. during the washes. An aliquot taken at this time was dried, stripped of solvent and analyzed by atomic absorption to contain 7 ppm palladium and less than 2 ppm copper. Sodium hydroxide pellets (3.5 kilograms) were added to the toluene solution and the temperature raised until reflux. Acetone was removed overhead as it formed. After 4.5 hours, all the acetone had been removed. The caustic was washed from the system with water until the washings were neutral. The toluene was stripped and the mixture of acetylene terminated sulfone resins was again analyzed for metals, and the palladium content was 9 ppm and the copper content was less than 2 ppm.

In order to further demonstrate the effectiveness of the metals separation process of the present invention, the following comparative tests were made. All washes are 50 milliliters in volume unless otherwise indicated.

EXAMPLE 24

A 250 milliliter, 3-necked round-bottomed flask equipped with a nitrogen inlet-outlet, magnetic stirrer, condenser and heating mantle was charged with 14.0 grams of 4,4'-bis-(3-bromophenoxy)diphenyl sulfone, 0.25 gram of triphenylphosphine, 0.05 gram of bis-triphenylphosphine palladium dichloride, 5 grams of methylbutynol and 50 milliliters of triethylamine. After purging with nitrogen, 0.05 gram of cuprous iodide was added and the mixture heated to reflux. When high performance liquid chromotograph of the samples indicated the reaction was complete, triethylamine hydrobromide was removed by filtration. The filtrate was stripped and the residue taken up in 150 milliliters of toluene. The resulting reaction mixture contains 1200 ppm copper and 500 ppm palladium.

In order to test the effectiveness of sulfuric acid in combination with ammonium hydroxide for metals separation, one sample of the solution was washed with 50 milliliter volumes of 10% aqueous sulfuric acid, water, concentrated ammonium hydroxide (four times) and finally water.

The resulting solution was dried over magnesium sulfate by placing the adsorbent (roughly 1-to-1 weight relationship with product) in a small fritted funnel, topping with a layer of celite, gravity filtration and then solvent wash. The toluene was removed under vacuum and a light yellow powder resulted. Analysis by atomic absorption indicated 38 ppm copper and 130 ppm palladium.

For comparative purposes, a second sample of the solution of the reaction mixture in toluene was washed with a 50 milliliter portion of 10% aqueous hydrochloric acid and then water. The resulting solution contained 31 ppm copper and 500 ppm palladium. Next, the solution was washed with concentrated ammonium hydroxide and then water, and the resulting solution contained 57 ppm palladium and less than 5 ppm copper. The solution was washed again with concentrated ammonium hydroxide and water, which further reduced the palladium level to 47 ppm. Finally, the solution was washed again with concentrated ammonium hydroxide at a temperature of 60° C. and then water, and the palladium level was reduced to 16 ppm and less than 5 ppm copper.

A third sample of the reaction solution was tested to determine the effect of substituting ethylenediamine for ammonium hydroxide. In this test, the reaction solution was washed with a 50 milliliter portion of 10% hydrochloric acid and twice with water. Next, the solution was washed with 50 milliliters of ethylenediamine at a temperature of 60° C. and then with water. Analysis of the resulting sample indicated that the palladium level was reduced to 18 ppm and the copper level was less than 5 ppm.

The foregoing tests show that the combination of a hydrogen halide and an amino-type complexing agent is required to lower both the copper and palladium contamination to acceptable levels.

EXAMPLE 25

Preparation of Dinitro-Acetylene Terminated Sulfone

One mole of hydroxybromophenoxydiphenyl sulfone, one liter of toluene and one liter of sulfolane are added to a three necked flask. Next, one mole of potassium hydroxide is added and the liberated water is removed as a toluene-water azeotrope. After all of the water has been removed, one liter of pyridine is added and one mole of 3,4-dinitrofluorobenzene is added at a temperature of 0° C.

The reaction is allowed to warm and then is heated at 60° C. to insure complete reaction. The product is then diluted with water and extracted with methylene chloride solvent, and the solvent is evaporated to yield the desired 4-(3,4-dinitrophenoxy)-4'-(3-ethynylphenoxy)-diphenylsulfone.

EXAMPLE 26

Preparation of Diamino-Acetylene Terminated Sulfone

Ten moles of sodium dithionite in 5 liters of water are added to a 10 liter erhlenmeyer flask equiped with a magnetic stirrer. Next, 10 moles of sodium hydroxide are added and then a solution of 4-(3,4-dinitrophenoxy)-4'-(3-ethynylphenoxy)diphenyl sulfone in methanol is added to the mixture. The solvent is then removed in vacuuo to yield the desired 4-(3,4-diaminophenoxy)-4'-(3-ethynylphenoxy)diphenyl sulfone.

Resort may be had to the variations and modifications as fall within the spirit of the invention and the scope of the appended claims.

We claim:

1. A process for the production of an acetylene terminated sulfone which comprises:
    (a) reacting a sulfonyldiphenol with a material selected from the group consisting of a meta-dibromobenzene, a para-dibromobenzene and mixtures thereof in the presence of a potassium base to form a bis-bromophenoxydiphenyl sulfone;
    (b) reacting said bis-bromophenoxydiphenyl sulfone with a substituted terminal acetylene compound containing at least three carbon atoms and an hydroxy group on the carbon atom adjacent to the acetylene group to form the corresponding hydroxy-acetylene terminated phenoxydiphenyl sulfone; and
    (c) subjecting said hydroxy-acetylene terminated phenoxydiphenyl sulfone to base catalyzed cleavage to form the corresponding acetylene terminated sulfone.

2. The process of claim 1, wherein said sulfonyldiphenol is 4,4'-sulfonyldiphenol.

3. The process of claim 1, wherein the dibromobenzene is a mixture of meta- and para-dibromobenzene.

4. The process of claim 1, wherein said potassium base is potassium hydroxide.

5. The process of claim 1, wherein said sulfonyldiphenol and said dibromobenzene are reacted in the presence of a catalytic amount of a copper salt.

6. The process of claim 5, wherein said copper salt is cuprous chloride, cuprous iodide, copper stearate, copper or cuprous bromide.

7. The process of claim 6, wherein said copper salt is cuprous chloride.

8. The process of claim 1, wherein said substituted terminal acetylene compound has the formula:

$$H\!-\!C\!\equiv\!C\!-\!Z$$

wherein Z represents the moiety:

wherein $R^2$ and $R^3$ can be the same or different and are selected from the group consisting of hydrogen and lower alkyl groups having from one to 4 carbon atoms, phenyl and substituted phenyl, and wherein $R^2$ and $R^3$ when taken together with the carbon atom to which they are attached form a saturated 5- or 6-membered ring.

9. The process of claim 8, wherein said terminal acetylene compound is 3-methylbutyn-3-ol, 2-methyl-3-butyn-2-ol, 3-methyl-1-pentyn-3-ol.

10. The process of claim 9, wherein said terminal acetylene compound is 3-methyl-butyn-3-ol.

11. The process of claim 1, wherein said sulfonyldiphenol and said dibromobenzene are reacted at a temperature in the range of between 100° to about 250° C.

12. The process of claim 11, wherein said temperature is in the range of between about 140° and about 200° C.

13. The process of claim 1, wherein said sulfonyldiphenol and dibromobenzene are reacted in the presence of a solvent.

14. The process of claim 13, wherein said solvent is tetrahydrothiophene 1,1-dioxide, dimethylsulfoxide, N-methylpyrolidone or bis-methoxy ethoxy diethyl ether.

15. The process of claim 14, wherein said solvent is tetrahydrothiophene 1,1-dioxide.

16. A process for the production of a bis-bromophenoxydiphenyl sulfone which comprises reacting a sulfonyldiphenol with a material selected from the group consisting of a meta-dibromobenzene, a para-dibromobenzene and mixtures thereof in the presence of a potassium base to form said bis-bromophenoxydiphenyl sulfone.

17. The process of claim 16, wherein said sulfonyldiphenol and dibromobenzene are reacted in the presence of a solvent.

18. The process of claim 16, wherein said sulfonyldiphenol is 4,4'-sulfonyldiphenol.

19. The process of claim 16, wherein the dibromobenzene is a mixture of meta- and para-dibromobenzene.

20. The process of claim 16, wherein said potassium base is potassium hydroxide.

21. The process of claim 16, wherein said sulfonyldiphenol and said dibromobenzene are reacted in the presence of a catalytic amount of a copper salt.

22. The process of claim 21, wherein said copper salt is cuprous chloride, cuprous iodide, copper stearate, copper acetate, copper acetonylacetonate or cuprous bromide.

23. The process of claim 22, wherein said copper salt is cuprous chloride.

24. The process of claim 22, wherein the amount of said copper salt employed is from about 0.1 to about 10 mole percent.

25. The process of claim 24, wherein the amount of said copper salt employed is from about 1.0 to about 5.0 mole percent.

26. The process of claim 16, wherein said sulfonyldiphenol and said dibromobenzene are reacted at a temperature in the range of between about 100° and about 250° C.

27. The process of claim 26, wherein said temperature is in the range of between about 140° and about 200° C.

28. The process of claim 17, wherein said solvent is tetrahydrothiophene 1,1-dioxide, dimethylsulfoxide, N-methylprolidone or bis-methoxy ethoxy diethyl ether.

29. The process of claim 28, wherein said solvent is tetrahydrothiophene 1,1-dioxide.

30. The process of claim 16, wherein the reaction time is from about 1 to about 150 hours.

31. The process of claim 30, wherein the reaction time is from about 3 to about 24 hours.

32. A process for the production of an hydroxy-acetylene terminated phenoxydiphenyl sulfone which comprises reacting a bis-bromophenoxydiphenyl sulfone, wherein the bromine and oxygen moieties attached directly to the same phenyl nucleus are either meta or para, with a substituted terminal acetylene compound containing at least three carbon atoms and an hydroxy group on the carbon atom adjacent to the acetylene group having the formula:

$$H\!-\!C\!\equiv\!C\!-\!Z$$

wherein Z represents the moiety:

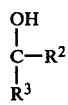

wherein $R^2$ and $R^3$ can be the same or different and are alkyl groups having from one to 4 carbon atoms, phenyl and substituted phenyl, and wherein $R^2$ and $R^3$ when taken together with the carbon atom to which they are attached form a saturated 5- or 6-membered ring.

33. The process of claim 32, wherein a solvent is employed wherein said solvent is an amine solvent having the formula:

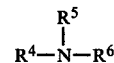

wherein $R^4$, $R^5$ and $R^6$ can be the same or different and are selected from the group consisting of hydrogen and lower alkyl groups having from one to 4 carbon atoms, with the proviso that no more than one of said R groups can be hydrogen.

34. The process of claim 32, wherein said substituted terminal acetylene compound is 3-methylbutyn-3-ol, 2-methyl-3-butyn-2-ol, 3-methyl-1-pentyn-3-ol, 3-ethyl-1-pentyn-3-ol, 2-phenyl-3-butyn-2-ol, 1-ethynylcyclohexanol or 1-ethynylcyclopentanol.

35. The process of claim 34, wherein said substituted terminal acetylene compound is 3-methylbutyn-3-ol.

36. The process of claim 33, wherein said amine solvent is dimethylamine, trimethylamine, diethylamine, triethylamine, ethylpropylamine, ethylbutylamine or dibutylamine.

37. The process of claim 36, wherein said amine solvent is triethylamine.

38. The process of claim 32, wherein a complex catalyst is employed wherein said catalyst is a palladium complex having the formula:

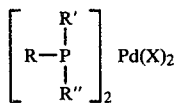

where X is bromine, iodine or chlorine, and R, R' and R" are the same or different and are selected from the group consisting of phenyl, alkyl groups having from 1 to 4 carbon atoms and substituted phenyl groups.

39. The process of claim 38, wherein said palladium complex is bis(triphenylphosphine)palladium dichloride, bis(triphenylphosphine)palladium dibromide, bis(tri-n-butylphosphine)palladium dichloride, bis(tri-t-butyl-phosphine)palladium dichloride, bis(tri-i-butyl-phosphine)palladium dichloride, bis(triethylphosphine)palladium dichloride, bis(tri-propylphosphine)palladium dichloride, bis(tritolylphosphine)palladium dichloride, bis(trianisylphosphine)palladium dichloride, bis(tri(chlorophenyl)phosphine)palladium dichloride or bis(tri(bromophenyl)phosphine)palladium dichloride.

40. The process of claim 38, wherein the amount of said palladium catalyst employed is from about 0.01 to about 1.0 mole percent.

41. The process of claim 40, wherein the amount of said palladium complex catalyst employed is from about 0.02 to about 0.05 mole percent.

42. The process of claim 38, wherein a promoter comprising a copper salt is employed.

43. The process of claim 42, wherein said copper salt is cuprous chloride, cuprous iodide, copper stearate, copper acetate, copper acetonylacetonate or cuprous bromide.

44. The process of claim 43, wherein said copper salt is cuprous chloride.

45. The process of claim 42, wherein the molar ratio of promoter to palladium complex is from about 0.5:1 to about 20:1.

46. The process of claim 45, wherein the molar ratio of promoter to palladium complex is from about 1:1 to about 5:1.

47. The process of claim 32, wherein the molar ratio of said bis-bromophenoxydiphenyl sulfone to said terminal acetylene compound is from about 1:0.5 to about 1:100.

48. The process of claim 47, wherein the molar ratio of said bis-bromophenoxydiphenyl sulfone to said terminal acetylene compound is from about 1:2 to about 1:5.

49. The process of claim 32, wherein the reaction temperature is from about 20° to about 200° C.

50. The process of claim 49, wherein the reaction temperature is from about 50° to about 125° C.

51. The process of claim 32, wherein the reaction time is from about 1 to about 150 hours.

52. The process of claim 51, wherein the reaction time is from about 3 to about 24 hours.

53. A process for the production of an acetylene terminated sulfone which comprises subjecting an hydroxy-acetylene terminated phenoxydiphenyl sulfone to base catalyzed cleavage to form said acetylene terminated sulfone.

54. The process of claim 53, wherein the base used in the base catalyzed cleavage is potassium hydroxide.

55. The process of claim 53, wherein the reaction temperature is from about 70° to about 130° C.

56. The process of claim 56, wherein the reaction temperature is from about 90° to about 120° C.

57. The process of claim 53, wherein the reaction time is from about 0.5 to about 10 hours.

58. The process of claim 57, wherein the reaction time is from about 1 to about 4 hours.

59. A process for the production of an acetylene terminated sulfone which comprises:
(a) reacting a sulfonyldiphenol with a material selected from the group consisting of a metadibromobenzene, a para-dibromobenzene and mixtures thereof in the presence of a sodium base to form an hydroxyphenylbromophenoxyphenyl sulfone;
(b) reacting said hydroxyphenylbromophenoxyphenyl sulfone with a substituted terminal acetylene compound containing at least three carbon atoms and an hydroxy group on the carbon atom adjacent to the acetylene group to form the corresponding hydroxy-acetylene phenoxyphenylhydroxyphenyl sulfone; and
(c) subjecting said hydroxy-acetylene phenoxyphenylhydroxyphenyl sulfone to base catalyzed cleavage to form the corresponding acetylene terminated sulfone.

60. The process of claim 59, wherein said sodium base is sodium hydroxide.

61. The process of claism 59, wherein said sulfonyldiphenol and said dibromobenzene are reacted in the presence of a catalytic amount of a copper salt.

62. The process of claim 59, wherein said sulfonyldiphenol is 4,4'-sulfonyldiphenol.

63. The process of claim 59, wherein the dibromobenzene is a mixture of meta- and para-dibromobenzene.

64. The process of claim 61, wherein said copper salt is cuprous chloride, cuprous iodide, copper stearate, copper acetate, copper acetonylacetonate or cuprous bromide.

65. The process of claim 64, wherein said copper salt is cuprous chloride.

66. The process of claim 59, wherein said substituted terminal acetylene compound has the formula:

wherein Z represents the moiety:

wherein $R^2$ and $R^3$ can be the same or different and are selected from the group consisting of hydrogen and lower alkyl groups having from 1 to 4 carbon atoms, phenyl and substituted phenyl, and wherein $R^2$ and $R^3$ can form a saturated 5- or 6-membered ring.

67. The process of claim 66, wherein said terminal acetylene compound is 3-methylbutyn-3-ol, 2-methyl-3-butyn-2-ol, 3-methyl-1-pentyn-3-ol, 3-ethyl-1-pentyn-3-ol, 2-phenyl-3-butyn-2-ol, 1-ethynylcyclohexanol or 1-ethynylcyclopentanol.

68. The process of claim 67, wherein said terminal acetylene compound is 3-methyl-butyn-3-ol.

69. The process of claim 59, wherein said sulfonyldiphenol and said dibromobenzene are reacted at a temperature in the range of between about 100° and about 250° C.

70. The process of claim 69, wherein said temperature is in the range of between about 140° and about 200° C.

71. The process of claim 59 wherein said sulfonyldiphenol and dibromobenzene are reacted in the presence of a solvent.

72. The process of claim 71, wherein said solvent is tetrahydrothiophene 1,1-dioxide, dimethylsulfoxide, N-methylprolidone or bis-methoxy ethoxy diethyl ether.

73. The process of claim 72, wherein said solvent is tetrahydrothiophene 1,1-dioxide.

74. A process for the production of an hydroxyphenylbromophenoxyphenyl sulfone which comprises reacting a sulfonyldiphenol with a material selected from the group consisting of a meta-dibromobenzene, a para-dibromobenzene and mixtures thereof in the presence of a sodium base to form an hydroxyphenylbromophenoxyphenyl sulfone.

75. The process of claim 74, wherein said sulfonyldiphenol and said dibromobenzene are reacted in the presence of a catalytic amount of a copper salt.

76. The process of claim 74, wherein said copper salt is cuprous chloride, cuprous iodide, copper stearate, copper acetate, copper acetonylacetonate or cuprous bromide.

77. The process of claim 74, wherein said sulfonyldiphenol is 4,4'-sulfonyldiphenol.

78. The process of claim 74, wherein the dibromobenzene is a mixture of meta- and para-dibromobenzene.

79. The process of claim 74, wherein said sodium base is sodium hydroxide.

80. The process of claim 76, wherein said copper salt is cuprous chloride.

81. The process of claim 75, wherein the amount of said copper salt employed is from about 0.1 to about 10 mole percent.

82. The process of claim 81, wherein the amount of said copper salt employed is from about 1.0 to about 5.0 mole percent.

83. The process of claim 74, wherein said sulfonyldiphenol and said dibromobenzene are reacted at a temperature in the range of between about 100° and about 250° C.

84. The process of claim 83, wherein said temperature is in the range of between about 140° and about 200° C.

85. The process of claim 74, wherein said sulfonyldiphenol and dibromobenzene are reacted in the presence of a solvent.

86. The process of claim 85, wherein said solvent is tetrahydrothiophene 1,1-dioxide, dimethylsulfoxide, N-methylprolidone or bis-methoxy ethoxy diethyl ether.

87. The process of claim 84, wherein said solvent is tetrahydrothiophene 1,1-dioxide.

88. The process of claim 74, wherein the reaction time is from about 1 to about 150 hours.

89. The process of claim 88, wherein the reaction time is from about 3 to about 24 hours.

90. A process for the production of an hydroxy-acetylene terminated phenoxyphenylhydroxyphenyl sulfone which comprises reacting an hydroxyphenylbromophenoxyphenyl sulfone with a substituted terminal acetylene compound having the formula:

H—C≡C—Z wherein Z represents the moiety:

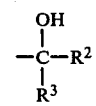

wherein $R^2$ and $R^3$ can be the same or different and are selected from the group consisting of hydrogen and lower alkyl groups having from one to 4 carbon atoms, phenyl and substituted phenyl, and wherein $R^2$ and $R^3$ can form a saturated 5- or 6-membered ring.

91. The process of claim 90, wherein a solvent is employed wherein said solvent is an amine solvent having the formula:

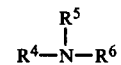

wherein $R^4$, $R^5$ and $R^6$ can be the same or different and are selected from the group consisting of hydrogen and lower alkyl groups having from one to 4 carbon atoms, with the proviso that no more than one of said R groups can be hydrogen.

92. The process of claim 90, wherein said substituted terminal acetylene compound is 3-methylbutyn-3-ol, 2-methyl-3-butyn-2-ol, 3-methyl-1-pentyn-3-ol, 3-ethyl-1-pentyn-3-ol, 2-phenyl-3-butyn-2-ol, 1-ethynylcyclohexanol or 1-ethynylcyclopentanol.

93. The process of claim 92, wherein said substituted terminal acetylene compound is 3-methylbutyn-3-ol.

94. The process of claim 91, wherein said amine solvent is dimethylamine, trimethylamine, diethylamine, triethylamine, ethylpropylamine, ethylbutylamine or dibutylamine.

95. The process of claim 94, wherein said amine solvent is triethylamine.

96. The process of claim 90, wherein a complex catalyst is employed wherein said catalyst is a palladium complex having the formula:

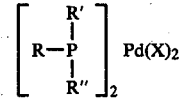

where X is bromine, iodine or chlorine, and R, R' and R" are the same or different and are selected from the group consisting of phenyl, alkyl groups having from 1 to 4 carbon atoms and substituted phenyl groups.

97. The process of claim 96, wherein said palladium complex is bis(triphenylphosphine)palladium dichloride, bis(triphenylphosphine)palladium dibromide, bis(tri-n-butylphosphine)palladium dichloride, bis(tri-t-butyl-phosphine)palladium dichloride, bis(tri-i-butylphosphine)palladium dichloride, bis(triethylphosphine)palladium dichloride, bis(tripropylphosphine)palladium dichloride, bis(tritolylphosphine)palladium dichloride, bis(trianisylphosphine)palladium dichloride, bis(tri(chlorophenyl))palladium dichloride or bis(tri(bromophenyl))phosphine)palladium dichloride.

98. The process of claim 96, wherein the amount of said palladium catalyst employed is from about 0.01 to about 1.0 mole percent.

99. The process of claim 98, wherein the amount of said palladium complex catalyst employed is from about 0.02 to about 0.05 mole percent.

100. The process of claim 96, wherein a promoter comprising a copper salt is employed.

101. The process of claim 100, wherein said copper salt is cuprous chloride, cuprous iodide, copper stearate, copper acetonate, copper acetonylacetonte or cuprous bromide.

102. The process of claim 101, wherein said copper salt is cuprous chloride.

103. The process of claim 100, wherein the molar ratio of promoter to palladium complex is from about 0.5:1 to about 20:1.

104. The process of claim 103, wherein the molar ratio of promoter to palladium complex is from about 1:1 to about 5:1.

105. The process of claim 90, wherein the molar ratio of said hydroxyphenylbromophenoxyphenyl sulfone to said terminal acetylene compound is from about 1:0.5 to about 1:100.

106. The process of claim 105, wherein the molar ratio of said hydroxyphenylbromophenoxyphenyl sulfone to said terminal acetylene compound is from about 1:1 to about 1:5.

107. The process of claim 90, wherein the reaction temperature is from about 20° to about 200° C.

108. The process of claim 107, wherein the reaction temperature is from about 50° to about 125° C.

109. The process of claim 90, wherein the reaction time is from about 1 to about 150 hours.

110. The process of claim 109, wherein the reaction time is from about 3 to about 24 hours.

111. A process for the production of an hydroxyacetylene terminated sulfone which comprises subjecting an hydroxy-acetylene terminated phenoxyphenylhydroxyphenyl sulfone to base catalyzed cleavage to form said acetylene terminated sulfone.

112. The process of claim 111, wherein the base used in the base catalyzed cleavage is potassium hydroxide.

113. The process of claim 111, wherein the reaction temperature is from about 70° to about 130° C.

114. The process of claim 113, wherein the reaction temperature is from about 90° to about 120° C.

115. The process of claim 111, wherein the reaction time is from about 0.5 to about 10 hours.

116. The process of claim 115, wherein the reaction time is from about 1 to about 4 hours.

117. A process for the production of bis-bromophenoxydiphenyl sulfone which comprises reacting a hydroxyphenylbromophenoxyphenyl sulfone with a material selected from the group consisting of a meta-dibromobenzene, a para-dibromobenzene and mixtures thereof in the presence of a potassium base to produce a bis-bromophenoxydiphenyl sulfone.

118. The process of claim 117, wherein said potassium base is potassium hydroxide.

119. The process of claim 117, wherein said hydroxyphenylbromophenoxyphenyl sulfone is reacted with para-dibromobenzene.

120. The process of claim 117, wherein said hydroxyphenylbromophenoxyphenyl sulfone is 4-hydroxy-4'-(3-bromophenoxy)diphenyl sulfone.

121. The process of claim 119, wherein said hydroxyphenylbromophenoxyphneyl sulfone is 4-hydroxy-4'-(3-bromophenoxy)diphenyl sulfone.

122. The process of claim 117, wherein said hydroxyphenylbromophenoxyphenyl sulfone and said dibromobenzene are reacted in the presence of a catalytic amount of a copper salt.

123. The process of claim 122, wherein said copper salt is cuprous chloride, cuprous iodide, copper stearate, copper acetonate, copper acetonylacetonate or cuprous bromide.

124. The process of claim 123, wherein said copper salt is cuprous chloride.

125. The process of claim 124, wherein the amount of said copper salt employed is from about 0.1 to about 10 mole percent.

126. The process of claim 125, wherein the amount of said copper salt employed is from about 1.0 to about 5.0 mole percent.

127. The process of claim 117, wherein said hydroxyphenylbromophenoxyphenyl sulfone and said dibromobenzene are reacted at a temperature in the range of between about 100° to about 250° C.

128. The process of claim 127, wherein said temperature is in the range of between about 140° and 200° C.

129. The process of claim 117, wherein said hydroxyphenylbromophenoxyphenyl sulfone and said dibromobenzene are reacted in the presence of a solvent.

130. The process of claim 129, wherein said solvent is tetrahydrothiophene 1,1-dioxide, dimethylsulfoxide, N-methylprolidone or bis-methoxy ethoxy diethyl ether.

131. The process of claim 130, wherein said solvent is tetrahydrothiophene 1,1-dioxide.

132. The process of claim 117, wherein the reaction time is from about 1 to about 150 hours.

133. The process of claim 132, wherein the reaction time is from about 3 to about 24 hours.

134. A process for the production of an oligomeric bromophenoxydiphenyl sulfone, which comprises reacting an hydroxyphenylbromophenoxyphenyl sulfone with a bromophenoxydiphenyl sulfone, wherein each of said compounds contain the bromine and oxygen moieties attached directly to the phenyl nucleus in a meta or para configuration to form an oligomeric bromophenoxydiphenyl sulfone.

135. The process of claim 134, wherein said oligomeric bromophenoxydiphenyl sulfone is reacted with a substituted terminal acetylene compound containing at least three carbon atoms and an hydroxy group on the carbon atom adjacent the acetylene group to form the corresponding oligomeric hydroxy-acetylene terminated sulfones.

136. The process of claim 134, wherein the hydroxyphenylbromophenoxyphenyl sulfone is 4-hydroxy-4'-(3-bromophenoxy)diphenyl sulfone.

137. The process of claim 134, wherein the bis-bromophenoxydiphenyl sulfone is 4,4'-bis-(3-bromophenoxy)diphenyl sulfone.

138. The process of claim 135, wherein the substituted terminal acetylene compound has the formula:

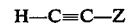

H—C≡C—Z wherein Z represents the moiety:

wherein $R^2$ and $R^3$ can be the same or different and are selected from the group consisting of hydrogen and lower alkyl groups having from 1 to 4 carbon atoms, phenyl and substituted phenyl, and wherein $R^2$ and $R^3$ when taken together with the carbon atom to which they are attached form a saturated 5- or 6-membered ring.

139. The process of claim 138, wherein $R^2$ and $R^3$ are each methyl.

140. The process of claim 135, wherein the base employed in the base catalyzed cleavage is potassium hydroxide.

141. The process of claim 135, wherein the temperature of the reaction is in the range from about 70° to about 130° C.

142. The process of claim 141, wherein the temperature of the reaction is in the range from about 90° to about 120° C.

143. The process of claim 135, wherein the reaction time is from about 0.5 to about 10 hours.

144. The process of claim 143, wherein the reaction time is from about 1 to about 4 hours.

145. The process of claim 135, wherein said oligomeric hydroxy-acetylene terminated sulfones are subjected to base catalyzed cleavage to form the corresponding oligomeric acetylene terminated sulfones.

* * * * *

UNITED STATES PATENT OFFICE
CERTIFICATE OF CORRECTION

Patent No. 4,356,325　　　　　　　　　Dated Oct. 26, 1982

Inventor(s) James J. Harrison, Edward T. Sabourin and Charles M. Selwitz

It is certified that error appears in the above-identified patent and that said Letters Patent are hereby corrected as shown below:

Col. 23, line 30, after formula, insert the following:
　　　　--Diamino-acetylene Terminated Sulfone--;

Col. 27, Table I, under the heading "Sulfolane (ml.)",
　　　　across from Ex. 2, "400" should read -- $400^C$ --;

Col. 28, Table I, under the heading "BPDS/BPDS+ Oligomers (%)",
　　　　across from Ex. 4, "80.0" should read -- 80.8 --;

Col. 40, Claim 56, line 1, "process of claim 56" should read
　　　　-- process of claim 55 --;

Col. 40, Claim 61, line 28, "claism" should read -- claim --;

Col. 42, Claim 97, line 61, "chlorophenyl)palladium" should
　　　　read -- chlorophenyl)phosphine)palladium --.

Signed and Sealed this

Sixth　Day of September 1983

[SEAL]

Attest:

GERALD J. MOSSINGHOFF
　　　Attesting Officer　　　　Commissioner of Patents and Trademarks